US012233411B2

(12) United States Patent
Deng et al.

(10) Patent No.: US 12,233,411 B2
(45) Date of Patent: Feb. 25, 2025

(54) DETECTION CHIP, METHOD OF USING DETECTION CHIP AND REACTION SYSTEM

(71) Applicant: BOE TECHNOLOGY GROUP CO., LTD., Beijing (CN)

(72) Inventors: Ruijun Deng, Beijing (CN); Mengjun Hou, Beijing (CN); Zhukai Liu, Beijing (CN); Jing Yu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 744 days.

(21) Appl. No.: 17/430,854

(22) PCT Filed: Mar. 12, 2021

(86) PCT No.: PCT/CN2021/080523
§ 371 (c)(1),
(2) Date: Aug. 13, 2021

(87) PCT Pub. No.: WO2021/218450
PCT Pub. Date: Nov. 4, 2021

(65) Prior Publication Data
US 2022/0410149 A1 Dec. 29, 2022

(30) Foreign Application Priority Data
Apr. 30, 2020 (CN) .......................... 202010367934.4

(51) Int. Cl.
*B01L 3/00* (2006.01)
*A61L 27/16* (2006.01)
(Continued)

(52) U.S. Cl.
CPC ........... *B01L 3/502715* (2013.01); *B01L 7/52* (2013.01); *B01L 2300/0645* (2013.01);
(Continued)

(58) Field of Classification Search
CPC ............... B01L 3/502715; B01L 7/52; B01L 2300/0645; B01L 2300/0663;
(Continued)

(56) References Cited

U.S. PATENT DOCUMENTS 10,272,437 B2 4/2019 Kim et al.
2005/0230252 A1 10/2005 Tsai et al.
(Continued)

FOREIGN PATENT DOCUMENTS

CN 1922478 A 2/2007
CN 102899245 A 1/2013
(Continued)

OTHER PUBLICATIONS

Search Report issued for EP Application No. 21783121.3, mailed on Sep. 21, 2023, 6 pages.
(Continued)

*Primary Examiner* — Jennifer Wecker
*Assistant Examiner* — Oyeleye Alexander Alabi
(74) *Attorney, Agent, or Firm* — Raj S. Dave; Dave Law Group LLC

(57) ABSTRACT

A detection chip, a method of using a detection chip and a reaction system are provided. The detection chip includes a first substrate, a micro-chamber definition layer and a heating electrode. The micro-chamber definition layer is located on the first substrate and defines a plurality of micro-reaction chambers. The heating electrode is located on the first substrate and closer to the first substrate than the micro-chamber definition layer, and configured to release heat after being energized. The heating electrode includes a plurality of sub-electrodes, orthographic projections of the plurality of micro-reaction chambers on the first substrate overlap with orthographic projections of at least two of the plurality of sub-electrodes on the first substrate, and the at least two
(Continued)

of the plurality of sub-electrodes have different heating values per unit time after being energized.

19 Claims, 12 Drawing Sheets

(51) Int. Cl.
| | |
|---|---|
| A61L 27/56 | (2006.01) |
| B01F 23/00 | (2022.01) |
| B01F 23/41 | (2022.01) |
| B01F 101/23 | (2022.01) |
| B01L 7/00 | (2006.01) |
| B01L 9/00 | (2006.01) |
| B23Q 17/24 | (2006.01) |
| C07K 14/705 | (2006.01) |
| C08F 220/56 | (2006.01) |
| C08L 33/26 | (2006.01) |
| C12M 1/34 | (2006.01) |
| C12Q 1/04 | (2006.01) |
| C12Q 1/18 | (2006.01) |
| C12Q 1/686 | (2018.01) |
| G01N 1/31 | (2006.01) |
| G01N 21/17 | (2006.01) |
| G01N 21/3577 | (2014.01) |
| G01N 21/359 | (2014.01) |
| G01N 21/39 | (2006.01) |
| G01N 21/45 | (2006.01) |
| G01N 21/64 | (2006.01) |
| G01N 21/77 | (2006.01) |
| G01N 21/78 | (2006.01) |
| G01N 27/414 | (2006.01) |
| G01N 30/12 | (2006.01) |
| G01N 30/68 | (2006.01) |
| G01N 30/70 | (2006.01) |
| G01N 30/72 | (2006.01) |
| G01N 30/88 | (2006.01) |
| G01N 33/00 | (2006.01) |
| G01N 33/18 | (2006.01) |
| G01N 33/50 | (2006.01) |
| G01N 33/53 | (2006.01) |
| G01N 33/543 | (2006.01) |
| G01N 33/68 | (2006.01) |
| G01N 33/74 | (2006.01) |
| G01N 35/00 | (2006.01) |
| G01N 35/10 | (2006.01) |
| G06T 7/00 | (2017.01) |
| G06T 7/90 | (2017.01) |
| H10K 10/46 | (2023.01) |
| H10K 85/00 | (2023.01) |
| H10K 85/20 | (2023.01) |

(52) U.S. Cl.
CPC . *B01L 2300/0663* (2013.01); *B01L 2300/161* (2013.01); *B01L 2300/1827* (2013.01)

(58) Field of Classification Search
CPC ....... B01L 2300/161; B01L 2300/1827; B01L 3/50851; B01L 3/5088; B01L 2200/12; B01L 2200/147; B01L 3/502707; B01L 2300/0819; B01L 2300/0893; B01L 2300/165; B01L 2400/0406; C12M 1/00; C12M 1/36; C12M 1/42; G01N 33/50
See application file for complete search history.

(56) References Cited

U.S. PATENT DOCUMENTS

| | | | |
|---|---|---|---|
| 2006/0068431 | A1 | 3/2006 | Lee et al. |
| 2009/0186404 | A1 | 7/2009 | Kim et al. |
| 2010/0086991 | A1 | 4/2010 | Fish |
| 2014/0272927 | A1* | 9/2014 | Coursey ................. C12Q 1/686 435/6.12 |
| 2018/0093268 | A1* | 4/2018 | Meier .................. C23C 14/024 |
| 2019/0204262 | A1 | 7/2019 | Pang et al. |
| 2021/0237052 | A1 | 8/2021 | Wu et al. |
| 2021/0268504 | A1 | 9/2021 | Zhao et al. |

FOREIGN PATENT DOCUMENTS

| | | | |
|---|---|---|---|
| CN | 104593256 | A | 5/2015 |
| CN | 105073974 | A | 11/2015 |
| CN | 108226261 | A | 6/2018 |
| CN | 108816300 | A | 11/2018 |
| CN | 209741124 | U | 12/2019 |
| CN | 209974747 | U | 1/2020 |
| CN | 214361269 | U | 10/2021 |
| DE | 102010043030 | A1 | 5/2012 |
| EP | 1974816 | A1 | 10/2008 |
| JP | 2006170642 | A | 6/2006 |
| WO | 2020147203 | A1 | 7/2020 |

OTHER PUBLICATIONS

Office action issued for CN Application No. 202010367934.4, mailed on Dec. 13, 2023, 13 pages.
Zhu Qiang-Yuan et al. "Microfluidic Digital Chip for Absolute Quantification of Nucleic Acid Amplification", Chemical Journal of Chinese Universities, V01 . 34, Mar. 2013, 545-550, 6 pages.
Office action issued for JP Application No. 2021-568789, mailed on Dec. 17, 2024, 12 pages.

* cited by examiner

DETECTION CHIP, METHOD OF USING DETECTION CHIP AND REACTION SYSTEM

CROSS-REFERENCE TO RELATED APPLICATIONS

The present application is the U.S. National Stage Entry of PCT/CN2021/080523, filed on Mar. 12, 2021, which claims priority of Chinese Patent Application No. 202010367934.4, filed on Apr. 30, 2020, the entire disclosures of which are incorporated herein by reference as part of the disclosure of this application.

TECHNICAL FIELD

The embodiment of the present disclosure relates to a detection chip, a method of using a detection chip and a reaction system.

BACKGROUND

Polymerase Chain Reaction (PCR) is a molecular biological technique for amplifying specific DNA fragments, which can replicate tiny amounts of deoxyribonucleic acid (DNA) in huge quantities, to increase its quantity greatly. Different from traditional PCR technology, Digital Polymerase Chain Reaction (dPCR) chip technology fully dilutes nucleic acid samples, so that the number of target molecules (that is, DNA templates) in each reaction unit is less than or equal to 1, and PCR amplification is carried out on the target molecules in each reaction unit respectively. After amplification, the fluorescence signals of each reaction unit are statistically analyzed, thus realizing the absolute quantitative detection of single molecule DNA. Because dPCR has the advantages of high sensitivity, strong specificity, high detection throughput and accurate quantification, etc., it is widely used in clinical diagnosis, gene instability analysis, single-cell gene expression, environmental microbial detection and prenatal diagnosis, etc.

SUMMARY

At least one embodiment of the present disclosure provides a detection chip, the detection chip comprises: a first substrate; a micro-chamber definition layer, located on the first substrate and defining a plurality of micro-reaction chambers; a heating electrode, located on the first substrate and closer to the first substrate than the micro-chamber definition layer, configured to release heat after being energized, the heating electrode comprises a plurality of sub-electrodes, orthographic projections of the plurality of micro-reaction chambers on the first substrate overlap with orthographic projections of at least two of the plurality of sub-electrodes on the first substrate, and the at least two of the plurality of sub-electrodes have different heating values per unit time after being energized.

For example, in the detection chip provided by an embodiment of the present disclosure, the heating electrode is configured to allow a current to flow along a first direction after being energized, and the plurality of sub-electrodes are arranged at intervals along a second direction, and the second direction is perpendicular to the first direction, each of the plurality of sub-electrodes has two sides opposite to each other in the second direction, and the plurality of sub-electrodes comprise a first sub-electrode and at least one second sub-electrode, wherein the first sub-electrode has adjacent sub-electrode on only one of the two sides, and each of the at least one second sub-electrode has adjacent sub-electrodes on the two sides, and a resistance value of the second sub-electrode is larger than a resistance value of the first sub-electrode.

For example, in the detection chip provided by an embodiment of the present disclosure, a width of the second sub-electrode along the second direction is smaller than a width of the first sub-electrode along the second direction.

For example, in the detection chip provided by an embodiment of the present disclosure, a plurality of second sub-electrodes are provided, and the plurality of second sub-electrodes are arranged at intervals along the second direction, and in the second direction, resistance values of the plurality of second sub-electrodes decrease in sequence along a direction extending from a center of the heating electrode to an edge of the heating electrode.

For example, in the detection chip provided by an embodiment of the present disclosure, in the second direction, widths of the plurality of second sub-electrodes are sequentially increased in the direction extending from the center of the heating electrode to the edge of the heating electrode.

For example, in the detection chip provided by an embodiment of the present disclosure, a plurality of second sub-electrodes are provided, and the plurality of second sub-electrodes are arranged at intervals along the second direction, resistance values of the plurality of second sub-electrodes are substantially equal.

For example, in the detection chip provided by an embodiment of the present disclosure, widths of the plurality of second sub-electrodes along the second direction are substantially equal.

For example, in the detection chip provided by an embodiment of the present disclosure, a spacing distance between adjacent sub-electrodes is 1-200 microns.

For example, in the detection chip provided by an embodiment of the present disclosure, a cross section of at least one of the plurality of sub-electrodes is rectangular, trapezoidal, triangular or wavy, and the cross section is parallel to the first substrate.

For example, in the detection chip provided by an embodiment of the present disclosure, three or more sub-electrodes are provided.

For example, in the detection chip provided by an embodiment of the present disclosure, orthographic projections of the plurality of sub-electrodes on the first substrate are sequentially surrounded, and an orthographic projection of a sub-electrode except a sub-electrode located at a center of the heating electrode is annular, and the plurality of sub-electrodes are insulated from each other.

For example, in the detection chip provided by an embodiment of the present disclosure, the plurality of sub-electrodes are located in different layers or an identical layer.

For example, in the detection chip provided by an embodiment of the present disclosure, a cross section of at least one of the plurality of sub-electrodes is in a square ring shape, a circular ring shape or an elliptical ring shape, and the cross section is parallel to the first substrate.

For example, in the detection chip provided by an embodiment of the present disclosure, two or more sub-electrodes are provided.

For example, in the detection chip provided by an embodiment of the present disclosure, a material of the heating electrode is a transparent conductive material.

For example, the detection chip provided by an embodiment of the present disclosure further comprises an accommodation chamber, the plurality of micro-reaction chambers are located in the accommodation chamber, and the accommodation chamber has an arc boundary.

For example, in the detection chip provided by an embodiment of the present disclosure, the micro-chamber definition layer further defines a sample injection channel and a sample outlet channel, both of the sample injection channel and the sample outlet channel are communicated with the accommodation chamber, the arc boundary of the accommodation chamber is located at joints of the accommodation chamber and the sample injection channel, and the accommodation chamber and the sample outlet channel.

For example, in the detection chip provided by an embodiment of the present disclosure, a radian of the arc boundary is less than or equal to $\pi/2$.

For example, in the detection chip provided by an embodiment of the present disclosure, the sample injection channel and the sample outlet channel are located at opposite sides of the accommodation chamber, the arc boundary comprises a first arc boundary and a second arc boundary, wherein the sample injection channel is communicated with the accommodation chamber at the first arc boundary, and the sample outlet channel is communicated with the accommodation chamber at the second arc boundary.

For example, in the detection chip provided by an embodiment of the present disclosure, a length of the sample injection channel is 1000-10000 microns, and a length of the sample outlet channel is 1000-10000 microns.

For example, the detection chip provided by an embodiment of the present disclosure further comprises a control circuit layer and a first insulation layer laminated on the first substrate, the control circuit layer comprises a control circuit, the first insulation layer comprises a through hole, the heating electrode is provided on the first insulation layer, the control circuit is electrically connected with the heating electrode through the through hole, and the control circuit is configured to apply an electrical signal to the heating electrode to energize the heating electrode.

For example, in the detection chip provided by an embodiment of the present disclosure, the control circuit layer further comprises at least one connection electrode, the at least one connection electrode is not covered by the first insulation layer and exposed to air.

For example, in the detection chip provided by an embodiment of the present disclosure, in a case where the orthographic projections of the plurality of sub-electrodes on the first substrate are sequentially surrounded, a plurality of connection electrodes are provided, and the plurality of connection electrodes are divided into a plurality of groups, a plurality of groups of connection electrodes are in one-to-one correspondence with the plurality of sub-electrodes, and each of the plurality of groups of connection electrodes is configured to transmit an electrical signal to a corresponding sub-electrode through the control circuit.

For example, in the detection chip provided by an embodiment of the present disclosure, electrical signals transmitted by the plurality of groups of connection electrodes are different from each other.

For example, in the detection chip provided by an embodiment of the present disclosure, each of the plurality of groups of connection electrodes comprises two connection electrodes, and the two connection electrodes are located at two opposite sides of the detection chip, respectively.

For example, the detection chip provided by an embodiment of the present disclosure further comprises a reaction region and a peripheral region, the heating electrode and the plurality of micro-reaction chambers are located in the reaction region, and the connection electrode is located in the peripheral region.

For example, the detection chip provided by an embodiment of the present disclosure further comprises a hydrophilic layer and a second insulation layer, the hydrophilic layer covers at least a side wall and a bottom of each of the plurality of micro-reaction chambers, and the second insulation layer is disposed between the heating electrode and the micro-chamber definition layer.

For example, the detection chip provided by an embodiment of the present disclosure further comprises a second substrate, and the second substrate is provided opposite to the first substrate.

For example, in the detection chip provided by an embodiment of the present disclosure, the first substrate and the second substrate both comprise a glass substrate.

For example, the detection chip provided by an embodiment of the present disclosure further comprises a hydrophobic layer, the hydrophobic layer covers a side of the second substrate facing the first substrate.

For example, the detection chip provided by an embodiment of the present disclosure further comprises a sample injection port and a sample outlet port, the sample injection port and the sample outlet port both penetrate through the second substrate and the hydrophobic layer, and the sample injection port and the sample outlet port are located at two opposite sides of the plurality of micro-reaction chambers.

For example, the detection chip provided by an embodiment of the present disclosure further comprises a bonding layer, the bonding layer is located between the first substrate and the second substrate, and a space surrounded by the bonding layer, the second substrate and the micro-chamber definition layer is the accommodation chamber.

For example, in the detection chip provided by an embodiment of the present disclosure, the bonding layer is made of thermosetting adhesive or photosensitive adhesive containing a spacer.

At least one embodiment of the present disclosure provides a reaction system, the reaction system comprises a control device and the detection chip according to any embodiment of the present disclosure, the control device is electrically connected with the detection chip and is configured to apply an electrical signal to the detection chip.

At least one embodiment of the present disclosure provides a method of using the detection chip any embodiment of the present disclosure, the method comprises: making reaction system solution enter the plurality of micro-reaction chambers; and energizing the heating electrode to release heat.

BRIEF DESCRIPTION OF THE DRAWINGS

In order to explain the technical scheme of the embodiments of the present disclosure more clearly, the drawings of the embodiments will be briefly introduced below. Obviously, the drawings in the following description only refer to some embodiments of the present disclosure, but do not limit the present disclosure.

DETAILED DESCRIPTION

Figure 1:
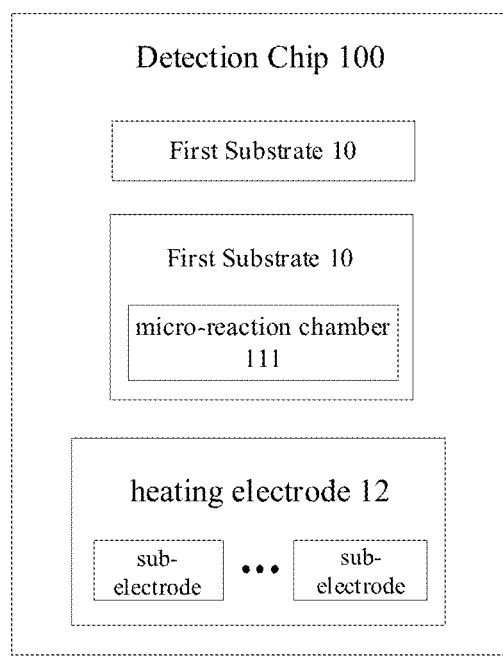
FIG. 1 is a schematic block diagram of a detection chip provided by some embodiments of the present disclosure.

In order to make objects, technical details and advantages of the embodiments of the invention apparent, the technical solutions of the embodiment will be described in a clearly and fully understandable way in connection with the drawings related to the embodiments of the invention. It is obvious that the described embodiments are just a part but not all of the embodiments of the invention. Based on the described embodiments herein, those skilled in the art can obtain other embodiment(s), without any inventive work, which should be within the scope of the invention.

Unless otherwise defined, all the technical and scientific terms used herein have the same meanings as commonly understood by one of ordinary skill in the art to which the present disclosure belongs. The terms, such as "first," "second," or the like, which are used in the description and the claims of the present disclosure, are not intended to indicate any sequence, amount or importance, but for distinguishing various components. The terms, such as "comprise/comprising," "include/including," or the like are intended to specify that the elements or the objects stated before these terms encompass the elements or the objects and equivalents thereof listed after these terms, but not preclude other elements or objects. The terms, such as "connect/connecting/connected," "couple/coupling/coupled" or the like, are not limited to a physical connection or mechanical connection, but may include an electrical connection/coupling, directly or indirectly. The terms, "on," "under," "left," "right," or the like are only used to indicate relative position relationship, and when the position of the object which is described is changed, the relative position relationship may be changed accordingly.

During the PCR reaction, the double-stranded structure of a DNA fragment denatured at high temperature to form a single-stranded structure, while the primer and a single strand are combined according to the principle of base complementary pairing at low temperature, and the base combination extension is realized at the optimum temperature of DNA polymerase. The above process is a temperature cycle process of denaturation-annealing-extension. A large number of DNA fragments can be replicated through a plurality of temperature cycle process of denaturation-annealing-extension.

In order to realize the above-mentioned temperature cycle process, it is usually necessary to use a series of external equipment to heat the detection chip, which makes the equipment bulky, the operation complex and the cost high. A conventional dPCR product is processed by using a silicon-based process, which makes it difficult for large-scale industrial production, and makes the detection chip expensive and the process complex. In order to improve the integration, a temperature control film layer (for example, a heating electrode) may be integrated in the detection chip. However, this kind of detection chip has some problems, such as poor thermal conductivity, uneven heat dissipation, etc., which makes the temperature in the center of the detection chip higher and the temperature in the edge lower. In order to position the micro-reaction chamber containing the reaction system solution in a part where the temperature controlling is uniform, it is necessary to design large-area blank regions, which are low-temperature regions at the edge, thus increasing the size of detection chip, limiting the increase of the number of micro-reaction chamber arrays, and making it difficult to achieve better temperature control effect.

In addition, because the detection chip is usually of micron-sized structure, the effect of the surface tension is significant during the sample injection process, resulting in obvious air residue. The residual air will disturb the reaction system solution during the temperature rise and fall of the detection chip, thus interfering with the detection result and reducing the accuracy of the detection result.

At least one embodiment of the present disclosure provides a detection chip, a method of using the detection chip and a reaction system. The detection chip can realize high-efficiency, accurate and uniform temperature control, so as to improve temperature uniformity, reduce an area of edge low-temperature region, effectively reduce the chip size, and increase the number of micro-reaction chambers. In addition, the detection chip is also compatible with semiconductor production lines, which can achieve large-scale standardized production. The detection chip provided by at least some embodiments can also realize uniform sample injection and reduce or avoid residual air, thereby reducing or avoiding the interference of bubbles on the detection result.

Hereinafter, embodiments of the present disclosure will be described in detail with reference to the drawings. It should be noted that the same reference numerals in different drawings will be used to refer to the same elements already described.

At least one embodiment of the present disclosure provides a detection chip, the detection chip includes a first substrate, a micro-chamber definition layer, and a heating electrode. The micro-chamber definition layer is located on the first substrate and defines a plurality of micro-reaction chambers. The heating electrode is located on the first substrate and closer to the first substrate than the micro-chamber definition layer, and is configured to release heat after being energized. The heating electrode comprises a plurality of sub-electrodes, orthographic projections of a plurality of micro-reaction chambers on the first substrate overlap with orthographic projections of at least two sub-electrodes on the first substrate, and at least two of the plurality sub-electrodes have different heating values per unit time after being energized.

FIG. 1 is a schematic block diagram of a detection chip provided by some embodiments of the present disclosure. For example, as shown in FIG. 1, the detection chip 100 includes a first substrate 10, a micro-chamber definition layer 11 and a heating electrode 12. The first substrate 10 plays a role of protection and support, and may be a glass substrate. The micro-chamber definition layer 11 is located on the first substrate 10 and defines a plurality of micro-reaction chambers 111. The heating electrode 12 is located on the first substrate 10 and closer to the first substrate 10 than the micro-chamber definition layer 11, and is configured to release heat after being energized.

For example, the heating electrode 12 includes a plurality of sub-electrodes. The orthographic projections of the plurality of micro-reaction chambers 111 on the first substrate 10 overlap with the orthographic projections of at least two sub-electrodes on the first substrate 10. For example, at least two of the plurality of sub-electrodes have different heating values per unit time after being energized. Here, the heating value per unit time refers to the heat released by the sub-electrode in unit time, and the unit time may be 1 second, 10 seconds, 1 minute, 10 minutes, etc., which is not limited by the embodiment of the present disclosure. For example, among a plurality of sub-electrodes, only two sub-electrodes may have different heating values per unit time, or three or four sub-electrodes may have different heating values per unit time, or all sub-electrodes may have different heating values per unit time, which is not limited by the embodiments of the present disclosure.

For example, the heating value per unit time of the sub-electrodes may be made different by using various ways. For example, in some examples, by making the resistance values of the sub-electrodes different, the heating value per unit time of the sub-electrodes under the condition of receiving the same electrical signal can be made different. For example, in other examples, the electrical signals received by the sub-electrodes may be made different, so that each sub-electrode may be controlled independently, and then the heating values per unit time are made different. Of course, the embodiments of the present disclosure are not limited to this, and other applicable ways may be adopted to make the heating value per unit time of the sub-electrodes different, which may be determined according to actual needs.

By making the heating values per unit time of the sub-electrodes different, the temperature of different regions in the detection chip 100 may be adjusted, which can realize highly efficient, accurate and uniform temperature control, improve the temperature uniformity, reduce the area of the edge low-temperature region, effectively reduce the chip size and increase the number of micro-reaction chambers.

For example, the detection chip 100 may be used for polymerase chain reaction (e.g., digital polymerase chain reaction), and may be further used for the detection process after the reaction. For example, the micro-reaction chamber 111 is used to contain the reaction system solution, and the heating electrode 12 releases heat after being energized, thereby heating the reaction system solution in the micro-reaction chamber 111 to perform amplification reaction.

Figure 2:
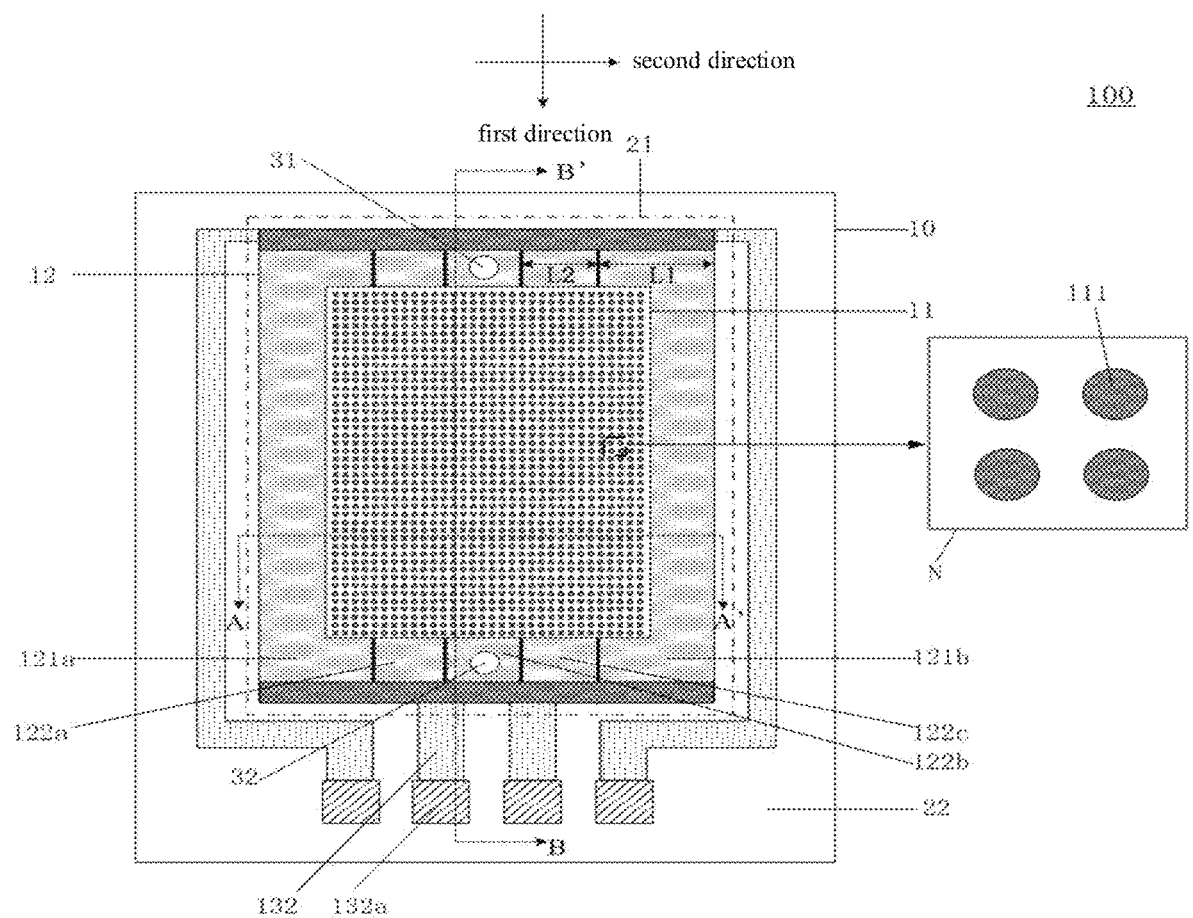
FIG. 2 is a schematic plan view of a detection chip provided by some embodiments of the present disclosure.
Figure 3:
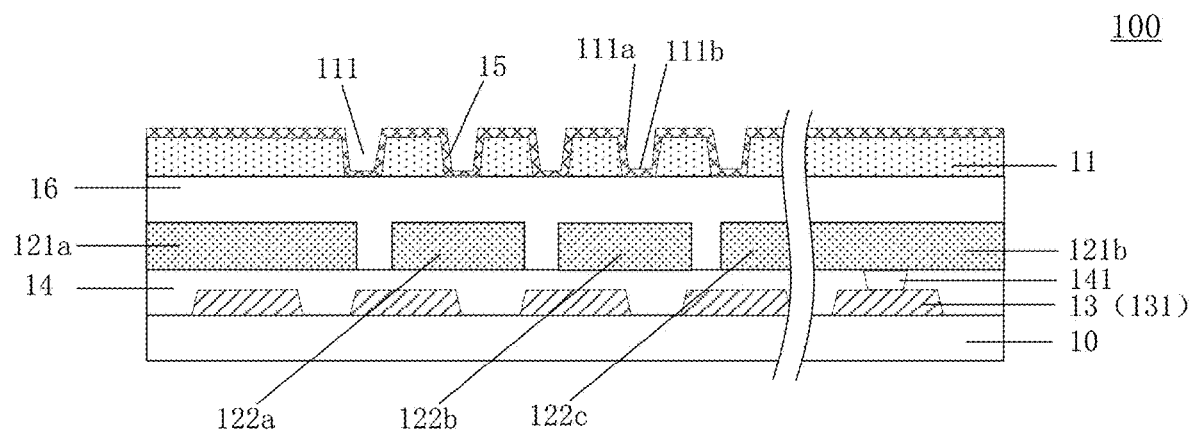
FIG. 3 is a schematic cross-sectional view of the detection chip shown in FIG. 2 along A-A'.
Figure 4:
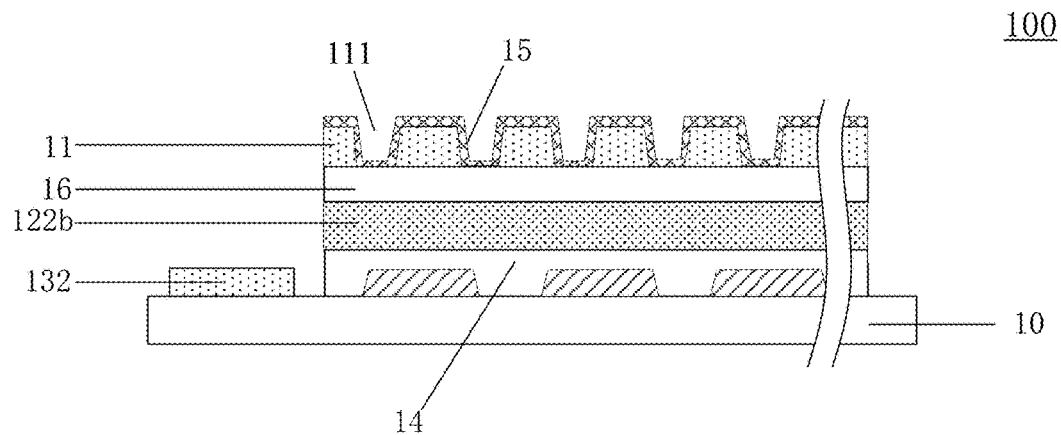
FIG. 4 is a schematic cross-sectional view of the detection chip shown in FIG. 2 along B-B'.

FIG. 2 is a schematic plan view of a detection chip provided by some embodiments of the present disclosure, FIG. 3 is a schematic cross-sectional view of the detection chip shown in FIG. 2 along A-A', and FIG. 4 is a schematic cross-sectional view of the detection chip shown in FIG. 2 along B-B'.

For example, as shown in FIG. 2, FIG. 3 and FIG. 4, in the detection chip 100, the micro-chamber definition layer 11 is located on the first substrate 10 and defines a plurality of micro-reaction chambers 111. Adjacent micro-reaction chambers 111 are at least partially spaced from each other (for example, by a partition wall). For example, each of the plurality of micro-reaction chambers 111 includes a sidewall 111a and a bottom 111b. The micro-reaction chamber 111 provides an accommodation space for the reaction system solution, and droplets of the reaction system solution entering the micro-cavity defining layer 11 and moving to the micro-reaction chamber 111 are relatively stably retained in the micro-reaction chamber 111. For example, the micro-reaction chamber 111 may be a micro-reaction groove, depression, etc., as long as it has a space capable of containing the reaction system solution, which is not limited by the embodiment of the present disclosure. For example, a depth of the micro-reaction groove or depression may be about 10 microns, or other suitable values.

For example, shapes of the plurality of micro-reaction chambers 111 may be the same, and the stereo shape of each micro-reaction chamber 111 is, for example, an approximate frustum, that is, as shown in the partial enlarged view N in FIG. 3, FIG. 4 and FIG. 2, the cross-section in the direction perpendicular to the first substrate 10 is approximately trapezoidal and the cross-section in the plane parallel to the first substrate 10 is approximately circular. It should be noted that at least some of the micro-reaction chambers 111 may have different shapes.

It should be noted that in the embodiment of the present disclosure, the shape of the micro-reaction chamber 111 is not limited and may be designed according to actual requirements. For example, the shape of each micro-reaction chamber 111 may be any suitable shape such as a cylinder, a cuboid, a polygonal prism, a sphere, an ellipsoid, etc. For example, the cross-sectional shape of the micro-reaction chamber 111 on a plane parallel to the first substrate 10 may be elliptical, triangular, polygonal, irregular, etc., and the cross-sectional shape in a direction perpendicular to the first substrate 10 may be square, circular, parallelogram, rectangular, etc.

For example, as shown in FIG. 2, a plurality of micro-reaction chambers 111 are uniformly distributed on the first substrate 10. For example, on the first substrate 10, a plurality of micro-reaction chambers 111 are arranged in an array. In this way, the fluorescence image obtained during the optical detection of the detection chip 100 in the subsequent stage can be more regular and orderly, so that the detection result can be obtained quickly and accurately. Of course, the embodiments of the present disclosure are not limited to this, and the plurality of micro-reaction chambers 111 may be unevenly distributed or arranged to be in the other arrangement manners on the first substrate 10, which is not limited by the embodiments of the present disclosure.

It should be noted that in the embodiment of the present disclosure, the size and number of the micro-reaction chambers 111 may be determined according to actual needs, and the size and number of the micro-reaction chambers 111 are related to the sizes of the detection chip 100 and the first substrate 10. When the size of the micro-reaction chambers 111 is unchanged, the larger the number of micro-reaction chambers 111, the larger the size of the detection chip 100 and the first substrate 10. For example, under the current preparation process, the number of micro-reaction chambers 111 may up to hundreds of thousands or even millions in an area of tens of square centimeters, and the detection flux of the detection chip 100 is large.

For example, the material of the micro-chamber definition layer 11 is photoresist, such as photoresist that can be performed the thick-film manufacturing, such as PS glue. The photoresist may be formed on the first substrate 10 by spin coating, and has a large thickness. For example, the micro-chamber definition layer 11 may be patterned and etched, to obtain a plurality of micro-reaction chambers 111 which are arranged at intervals.

For example, as shown in FIG. 2, FIG. 3 and FIG. 4, the heating electrode 12 is located on the first substrate 10, and the heating electrode 12 is closer to the first substrate 10 than the micro-chamber definition layer 11. The heating electrode 12 is configured to allow current to flow in a first direction to release heat after being energized. For example, both ends of the heating electrode 12 along the first direction can receive electrical signals (e.g., voltage signals or current signals), so that a current flowing along the first direction will be generated in the heating electrode 12. When a current flows through the heating electrode 12, heat is generated, and the heat is conducted to at least a portion of the micro-reaction chamber 111 for polymerase chain reaction.

It should be noted that, in the embodiment of the present disclosure, the first direction is not limited to a direction shown in FIG. 2, and may be other directions. When a position of the heating electrode 12 receiving the electrical signal changes, the first direction changes accordingly, which may be determined according to actual needs, and the embodiment of the present disclosure is not limited to this. The current flowing in the first direction means that the current substantially flows in the first direction, that is, the actual current flowing direction is substantially consistent with the first direction, for example, the angle between the actual current flowing direction and the first direction is acute angle.

For example, the heating electrode 12 may be made of a conductive material with high resistivity, so that the heating electrode 12 generates more heat when providing a small electrical signal, so as to improve the energy conversion rate. For example, the heating electrode 12 may be made of transparent conductive materials, such as indium tin oxide (ITO), tin oxide, etc. Since these transparent conductive materials not only have higher resistivity than metal materials, but also have transparency, so that these transparent conductive materials can realize heating while facilitate subsequent optical detection. Of course, the embodiments of the present disclosure are not limited to this, and the heating electrode 12 may also be made of other suitable materials, such as metal, and the embodiments of the present disclosure are not limited to this.

For example, the heating electrode 12 includes a plurality of sub-electrodes, such as sub-electrodes 121a, 121b, 122a, 122b, 122c. These sub-electrodes are, for example, planar electrodes. A plurality of sub-electrodes are arranged at intervals along a second direction, and the second direction is perpendicular to the first direction. In this example, for example, the sub-electrodes 121a, 122a, 122b, 122c, and 121b are sequentially distributed along the second direction with spacings between them. For example, the spacing distance between adjacent sub-electrodes is 1-200 microns, such as 1-20 microns, 1-15 microns, 1-10 microns or 1-5 microns. Since the spacing distance between the sub-electrodes is small relative to the size of the sub-electrodes themselves, the spacing between the sub-electrodes is indicated by a black line in FIG. 2. In this example, the number of sub-electrodes is five. It should be noted that in other examples, the number of sub-electrodes may be any number such as 3, 4, 6, etc., and is not limited to 5, as long as the number of sub-electrodes is greater than or equal to 3, which is not limited by the embodiment of the present disclosure.

For example, the orthographic projections of the plurality of micro-reaction chambers 111 on the first substrate 10 overlap with the orthographic projections of at least two sub-electrodes on the first substrate 10. Here, "orthographic projection" refers to projection on the first substrate 10 in a direction perpendicular to the first substrate 10. In this example, for example, the orthographic projections of the plurality of micro-reaction chambers 111 on the first substrate 10 overlap with all of the orthographic projections of the sub-electrodes 121a, 121b, 122a, 122b and 122c. Of course, the embodiments of the present disclosure are not limited to this. In other examples, the orthogonal projections of the plurality of micro-reaction chambers 111 on the first substrate 10 may also overlap with the orthogonal projections of any two sub-electrodes, any three sub-electrodes or any four sub-electrodes among the sub-electrodes 121a, 121b, 122a, 122b and 122c.

For example, each of the plurality of sub-electrodes has two opposite sides in the second direction. For example, as shown in FIG. 2, the two opposite sides may be the left side and the right side of each sub-electrode. The plurality of sub-electrodes include a first sub-electrode 121a, a first sub-electrode 121b, a second sub-electrode 122a, a second sub-electrode 122b, and a second sub-electrode 122c. The first sub-electrode 121a and the first sub-electrode 121b have adjacent sub-electrodes on only one of the two sides, and the second sub-electrode 122a, the second sub-electrode 122b and the second sub-electrode 122c have adjacent sub-electrodes on both sides.

For example, in this example, as shown in FIG. 2, the first sub-electrode 121a only has an adjacent sub-electrode on the right side, and the adjacent sub-electrode is the second sub-electrode 122a. The first sub-electrode 121b only has an adjacent sub-electrode on the left side, and the adjacent sub-electrode is the second sub-electrode 122c. The second sub-electrode 122a has adjacent sub-electrodes on the left and right sides, and these adjacent sub-electrodes are the first sub-electrode 121a and the second sub-electrode 122b. The second sub-electrode 122b has adjacent sub-electrodes on the left and right sides, and these adjacent sub-electrodes are the second sub-electrode 122a and the second sub-electrode 122c. The second sub-electrode 122c has adjacent sub-electrodes on the left and right sides, and these adjacent sub-electrodes are the second sub-electrode 122b and the first sub-electrode 121b.

It should be noted that in the embodiment of the present disclosure, the first sub-electrode and the second sub-electrode are used to distinguish sub-electrodes located at different positions. As shown in FIG. 2, the leftmost sub-electrode 121a and the rightmost sub-electrode 121b are referred to as the first sub-electrodes, while other sub-electrodes 122a, 122b and 122c are referred to as the second sub-electrodes. That is, the sub-electrode located outside is called the first sub-electrode, and the sub-electrode that is not located outside is called the second sub-electrode. For example, the number of the first sub-electrodes is 2, which is because there are always two sub-electrodes located outside, such as the leftmost and rightmost (when the first direction and the second direction change, the orientation of the outside changes accordingly). For example, one or more second sub-electrodes may be provided, which may be determined according to actual requirements, and the embodiment of the present disclosure is not limited to this.

For example, the resistance value of the second sub-electrode is larger than that of the first sub-electrode. For example, the resistance value of any one of the second sub-electrode 122a, the second sub-electrode 122b and the second sub-electrode 122c is larger than that of any one of the first sub-electrode 121a, the first sub-electrode 121b, and the resistance value of each of the second sub-electrodes 122a, 122b and 122c may be equal or unequal, and the resistance value of each of the first sub-electrodes 121a and 121b may be equal or unequal. By making the resistance value of the second sub-electrode larger than that of the first sub-electrode, the heating value per unit time of the second sub-electrode may be made different from that of the first sub-electrode, for example, the heating value per unit time of the second sub-electrode may be made smaller than that of the first sub-electrode. At this time, the second sub-electrode and the first sub-electrode may receive the same electrical signal, for example.

For example, a width L2 of the second sub-electrode in the second direction is smaller than a width L1 of the first sub-electrode in the second direction. For example, in this example, as shown in FIG. 2, the widths of the second sub-electrode 122a, the second sub-electrode 122b, and the second sub-electrode 122c in the second direction are equal and are all L2; the widths of the first sub-electrode 121a and the first sub-electrode 121b in the second direction are equal and are all L1, L2<L1. By making the width of the second sub-electrode smaller than that of the first sub-electrode, the resistance value of the second sub-electrode may be made larger than that of the first sub-electrode under the condition of using the same material and the same film thickness. Therefore, the production process can be simplified and the production cost can be reduced.

It should be noted that, in the embodiment of the present disclosure, the resistance value of the second sub-electrode may be made larger than that of the first sub-electrode by other means, and is not limited to the above-mentioned means. For example, in some examples, the first sub-electrode and the second sub-electrode may be made of conductive materials with different resistivity, so that the resistance value of the second sub-electrode is larger than that of the first sub-electrode. At this time, the width and thickness of the first sub-electrode and the second sub-electrode may be the same. For example, in other examples, after the first sub-electrode and the second sub-electrode are prepared from the same conductive material (e.g., ITO), the second sub-electrode is treated by a material treating process (e.g., ion doping process), so as to increase the resistance value of the second sub-electrode. At this time, the width and thickness of the first sub-electrode and the second sub-electrode may be the same. For example, in still other examples, the first sub-electrode and the second sub-electrode may be arranged in different layers and prepared with different parameters, for example, different materials, different widths and thicknesses may be adopted, so that the resistance value of the second sub-electrode is larger than that of the first sub-electrode. With regard to the specific implementation of making the resistance value of the second sub-electrode larger than that of the first sub-electrode, it is not limited to the above-described methods, and any applicable method may be adopted, which is not limited by the embodiment of the present disclosure.

When an electrical signal is applied to the heating electrode 12, the resistance values of the first sub-electrode 121a and the first sub-electrode 121b are smaller, so that they can release more heat. The first sub-electrode 121a and the first sub-electrode 121b generate larger heat per unit time, so as to reduce the edge heat dissipation effect and raise the edge temperature of the heating electrode 12. The resistance values of the second sub-electrode 122a, the second sub-electrode 122b and the second sub-electrode 122c are large, so that less heat may be released. The second sub-electrode 122a, the second sub-electrode 122b and the second sub-electrode 122c generate less heat per unit time, so that the center temperature of the heating electrode 12 is not too high. At this time, the electrical signals received by the plurality of sub-electrodes are, for example, the same electrical signal to reduce the number of signals.

Therefore, the detection chip 100 provided by the embodiment of the present disclosure can realize high-efficiency, accurate and uniform temperature control, improve temperature uniformity, and solve the problems of high center temperature and low edge temperature of common detection chip, thereby reducing the area of edge low-temperature region, effectively reducing chip size and increasing the number of micro-reaction chambers. In addition, the detection chip 100 provided by the embodiment of the present disclosure can make a plurality of micro-reaction chambers 111 receive uniform heat, which not only helps to improve the efficiency of amplification reaction in the detection chip 100, but also helps to improve the accuracy of the detection result. The detection chip 100 can detect nucleic acid molecules extracted from body fluids such as blood and urine more simply, sensitively and non-invasively, and realize auxiliary diagnosis and treatment in the fields of single cell analysis, early cancer diagnosis and prenatal diagnosis.

Figure 5:
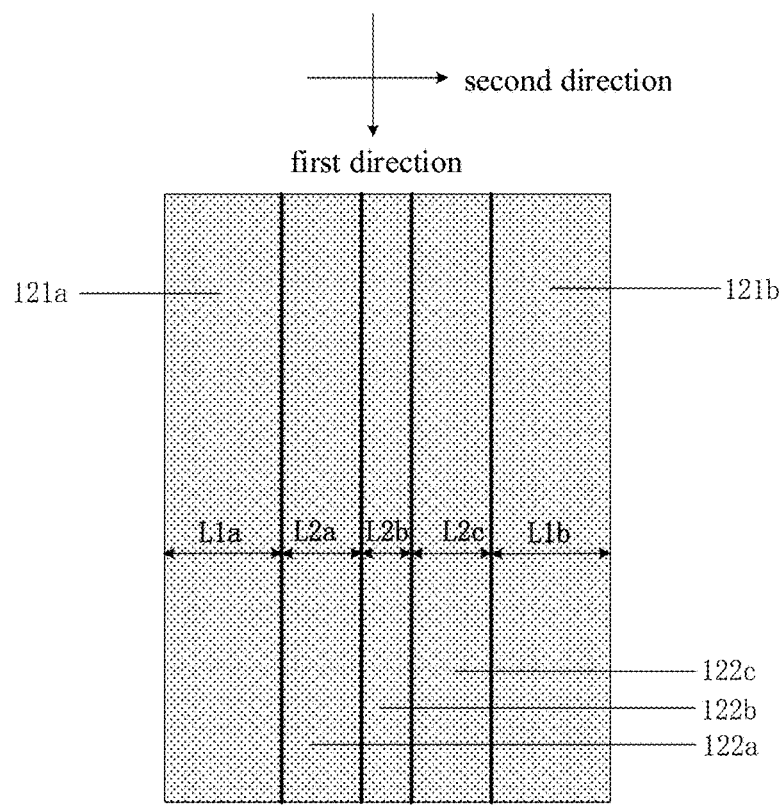
FIG. 5 is a schematic plan view of a heating electrode of a detection chip provided by some embodiments of the present disclosure.

FIG. 5 is a schematic plan view of a heating electrode of a detection chip provided by some embodiments of the present disclosure. In some examples, for example, as shown in FIG. 5, the at least one second sub-electrode includes a plurality of second sub-electrodes, that is, the second sub-electrode 122a, the second sub-electrode 122b and the second sub-electrode 122c, respectively. The second sub-electrode 122a, the second sub-electrode 122b and the second sub-electrode 122c are arranged at intervals along the second direction. In the second direction, the resistance values of the plurality of second sub-electrodes sequentially decrease in the direction extending from the center of the heating electrode 12 to the edge of the heating electrode 12. That is, the resistance value of the second sub-electrode 122b is larger than that of the second sub-electrode 122c, and the resistance value of the second sub-electrode 122b is also larger than that of the second sub-electrode 122a. For example, as shown in FIG. 5, in the direction extending from the center of the heating electrode 12 to the left edge, the resistance values of the second sub-electrodes decrease in sequence; similarly, in the direction extending from the center of the heating electrode 12 to the right edge, the resistance values of the second sub-electrodes decrease in sequence; the resistance value of the second sub-electrode (that is, the second sub-electrode 122b) located at the center of the heating electrode 12 is the largest. The resistance value of any one of the second sub-electrodes 122a, 122b and 122c is larger than that of any one of the first sub-electrodes 121a and 121b.

For example, in the second direction, in the direction extending from the center of the heating electrode 12 to the edge of the heating electrode 12, the widths of the plurality of second sub-electrodes in the second direction are sequentially increased. That is, a width L2b of the second sub-electrode 122b is smaller than a width L2c of the second sub-electrode 122c, and the width L2b of the second sub-electrode 122b is also smaller than a width L2a of the second sub-electrode 122a. For example, the width L2a of the second sub-electrode 122a and the width L2c of the second sub-electrode 122c may be equal or different. For example, as shown in FIG. 5, in the direction extending from the center of the heating electrode 12 to the left edge, the widths of the second sub-electrodes increase in sequence; similarly, in the direction extending from the center of the heating electrode 12 to the right edge, the widths of the second sub-electrodes increase in sequence; the width L2b of the second sub-electrode (that is, the second sub-electrode 122b) located at the center of the heating electrode 12 is the smallest. The width of any one of the second sub-electrodes 122a, 122b and 122c (i.e., any one of L2a, L2b and L2c) is smaller than that of any one of the first sub-electrodes 121a and 121b (i.e., any one of L1a and L1b).

Figure 6:
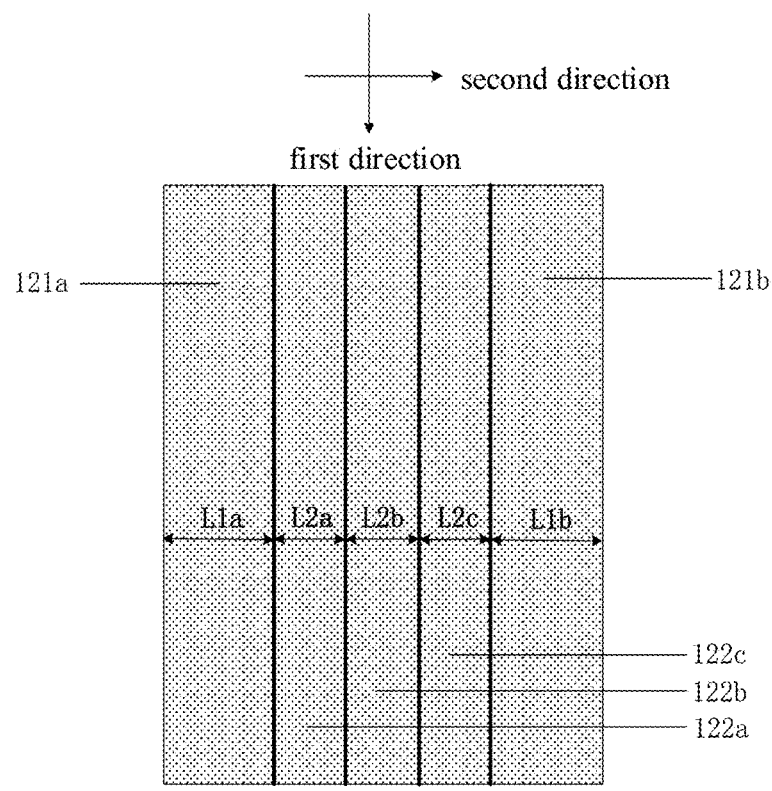
FIG. 6 is a schematic plan view of a heating electrode of another detection chip provided by some embodiments of the present disclosure.

FIG. 6 is a schematic plan view of a heating electrode of another detection chip provided by some embodiments of the present disclosure. In some examples, for example, as shown in FIG. 6, at least one second sub-electrode includes a plurality of second sub-electrodes, that is, the second sub-electrode 122a, the second sub-electrode 122b and the second sub-electrode 122c. The second sub-electrode 122a, the second sub-electrode 122b and the second sub-electrode 122c are arranged at intervals along the second direction. For example, the resistance values of the second sub-electrode 122a, the second sub-electrode 122b and the second sub-electrode 122c are substantially equal. Here, the "substantially equal" means that the difference between any two of the resistance values of the second sub-electrode 122a, the resistance value of the second sub-electrode 122b and the resistance value of the second sub-electrode 122c is less than a certain range, for example, less than 5% or 10%. Of course, "substantially equal" may also mean that the resistance values of the second sub-electrode 122a, the second sub-electrode 122b and the second sub-electrode 122c are completely equal. For example, the resistance value of any one of the second sub-electrodes 122a, 122b, and 122c is larger than that of any one of the first sub-electrodes 121a and 121b.

For example, the widths of the plurality of second sub-electrodes 122a, 122b, and 122c in the second direction are substantially equal. That is, the width L2a of the second sub-electrode 122a, the width L2b of the second sub-electrode 122b and the width L2c of the second sub-electrode 122c are substantially equal. Here, "substantially equal" means that the difference between any two of the widths L2a, L2b and L2c is less than a certain range, for example, less than 5% or 10%. Of course, "substantially equal" may also mean that the widths L2a, L2b and L2c are completely equal. For example, the width of any one of the second sub-electrodes 122a, 122b and 122c (i.e., any one of L2a, L2b and L2c) is smaller than that of any one of the first sub-electrodes 121a and 121b (i.e., any one of L1a and L1b).

It should be noted that in the embodiment of this disclosure, the relationship between the resistance values of a plurality of second sub-electrodes and the relationship between the resistance values of two first sub-electrodes may be determined according to actual needs, and the embodiment of the present disclosure is not limited to this. It is only necessary to ensure that the resistance value of any one of the second sub-electrodes is greater than the resistance value of any one of the first sub-electrodes.

Figure 7A:
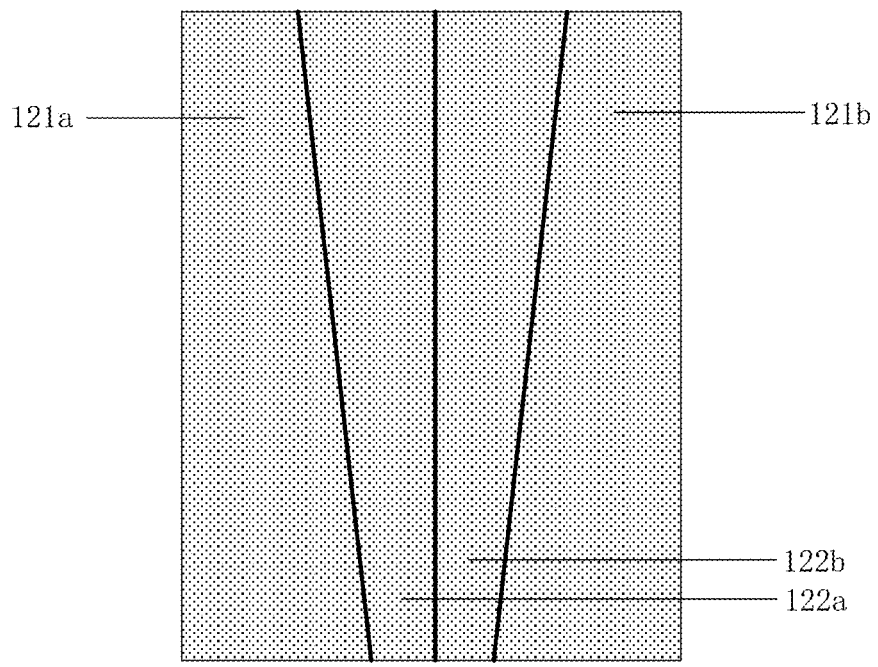
FIG. 7A is a schematic plan view of a heating electrode of another detection chip provided by some embodiments of the present disclosure.
Figure 7B:
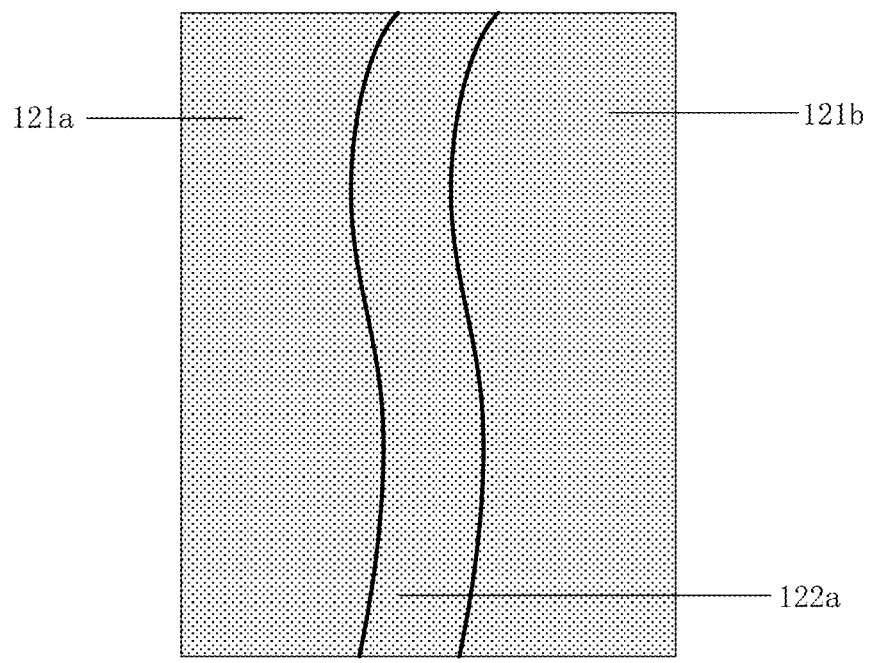
FIG. 7B is a schematic plan view of a heating electrode of another detection chip provided by some embodiments of the present disclosure.

For example, the cross section of at least one of the plurality of sub-electrodes is rectangular, trapezoidal, triangular or wavy, and the cross section is parallel to the first substrate 10. For example, in some examples, as shown in FIG. 2, FIG. 5, and FIG. 6, the cross-sectional shape of each sub-electrode is rectangular, that is, rectangular division design is adopted when patterning the heating electrode 12. For example, in other examples, as shown in FIG. 7A, the heating electrode 12 includes four sub-electrodes, and the cross-section shape of each sub-electrode is trapezoidal (e.g., right-angled trapezoidal). The average width of the first sub-electrodes 121a and 121b is larger, and the average width of the second sub-electrodes 122a and 122b is smaller. For example, in still other examples, as shown in FIG. 7B, the heating electrode 12 includes three sub-electrodes, and the cross-section shape of each sub-electrode is wavy, the width of the first sub-electrodes 121a and 121b is larger, and the width of the second sub-electrode 122a is smaller.

It should be noted that, in the embodiment of the present disclosure, the shape of the cross section of the sub-electrode is not limited, and may be any regular shape or irregular shape, that is, the heating electrode 12 may be patterned and divided in any suitable way, which may be determined according to actual needs. The cross-sectional shapes of the plurality of sub-electrodes may be the same or different, and the embodiments of the present disclosure are not limited to this. The size of the sub-electrode is not limited, which may be determined according to actual requirements, for example, according to the size of the detection chip.

For example, in some embodiments, as shown in FIG. 2, FIG. 3 and FIG. 4, the detection chip 100 further includes a control circuit layer 13 and a first insulation layer 14 laminated on the first substrate 10, and further includes a hydrophilic layer 15, a second insulation layer 16, at least one sample injection port 31 and at least one sample outlet port 32.

For example, the control circuit layer 13 is provided on the first substrate 10. The control circuit layer 13 includes a control circuit 131 configured to apply an electrical signal to the heating electrode 12 to energize the heating electrode 12. After receiving the electric signal, the heating electrode 12 may generate heat under the action of the electric signal, thereby heating the micro-reaction chamber 111. For example, the control circuit 131 may include one or more components of a switching transistor(s), a wire(s), an amplification circuit(s) and a processing circuit(s), and may also include any other applicable circuit element and structure, which are not limited by the embodiments of the present disclosure.

It should be noted that in FIG. 3 and FIG. 4, the control circuit layer 13 (control circuit 131) is shown as a plurality of separate parts (for example, a plurality of diagonal block regions shown in the figure), but this is only to show that the control circuit layer 13 may include a plurality of different circuit elements and structures, and does not mean that this is the actual structure of the control circuit layer 13. For example, the control circuit layer 13 may actually be a multi-layer structure, and a switching transistor(s), a wire(s), a resistor(s), a capacitor(s) or other suitable circuit structure(s) may be arranged in the multi-layer structure, which may be determined according to actual requirements and the embodiments of the present disclosure are not limited to this. The control circuit layer 13 may be made of any suitable materials, such as metal, transparent conductive material, semiconductor material, insulating material, etc., and these materials form the multi-layer structure by a plurality of processes, thereby forming the control circuit layer 13 and the control circuit 131 therein.

The first insulation layer 14 is disposed on the first substrate 10 and covers the control circuit layer 13. The heating electrode 12 is disposed on the first insulation layer 14. The first insulation layer 14 includes a through hole 141 penetrating through the first insulation layer 14, and the control circuit 131 is electrically connected with the heating electrode 12 through the through hole 141. A shape of the through hole 141 may be cylindrical, truncated cone, or the like. For example, the specific location of the through hole 141 is not limited, and may be determined according to actual requirements, for example, according to the layout design of the control circuit 131. The first insulation layer 14 provides insulation isolation for a necessary position of the control circuit layer 13 and the heating electrode 12, and provides a flat surface, to facilitate the heating electrode 12 to be arranged on the first insulation layer 14. The first insulation layer 14 may be made of an inorganic insulating material or an organic insulating material. For example, the material of the first insulation layer 14 is silicon dioxide or silicon nitride.

For example, as shown in FIG. 2 and FIG. 4, the control circuit layer 13 further includes at least one connection electrode 132 which is not covered by the first insulation layer 14 and exposed to the air. The connection electrode 132 is used for electrically connecting with a separately provided device, to receive an electrical signal and transmit the electrical signal to the control circuit 131. For example, when the connection electrode 132 is made of a metal material, the connection electrode 132 may be treated by electroplating, thermal spraying or vacuum plating, so as to form a metal protective layer on the surface of the connection electrode 132 to prevent the connection electrode 132 from being oxidized without affecting its conductivity.

For example, in this example, as shown in FIG. 2, the control circuit layer 13 includes four connection electrodes 132. The leftmost connection electrode 132 and the rightmost connection electrode 132 are respectively connected to wires surrounding the heating electrode 12, and the wires are electrically connected to one end of the heating electrode 12 through one or more through holes in the first insulation layer 14. The two connection electrodes 132 located in the middle are electrically connected to the other end of the heating electrode 12 through one or more through holes in the first insulation layer 14. When an electrical signal is applied, a current flowing in the first direction is generated in the heating electrode 12.

For example, the connection electrode 132 may also include a contact part 132a (for example, a Pad region as shown in FIG. 2), and the contact part 132a is not covered by the first insulation layer 14. For example, the contact portion 132a has a large square shape, so that the contact part 132a can be conveniently contacted and connected with a probe or an electrode in a device provided separately, and the contact area of the contact part 132a is large, so as to stably receive electrical signals. In this way, the detection chip 100 can be plug-and-play with simple operation and convenient use.

It should be noted that, in the embodiment of the present disclosure, the number of connection electrodes 132 is not limited, and may be one or more, which may be determined according to actual requirements, for example, according to the number of signals to be received and the degree of reliability to be achieved.

For example, as shown in FIG. 2, the detection chip 100 includes a reaction region 21 and a peripheral region 22. The heating electrode 12 and the plurality of micro-reaction chambers 111 are located in the reaction region 21, and the connection electrode 132 is located in the peripheral region 22. For example, the reaction region 21 is complementary to the peripheral region 22, and the peripheral region 22 is a region in the detection chip 100 except the reaction region 21.

For example, as shown in FIG. 3 and FIG. 4, the hydrophilic layer 15 covers at least the side wall 111a and the bottom 111b of each of the plurality of micro-reaction chambers 111, and the hydrophilic layer 15 has hydrophilic and oleophobic properties. For example, the hydrophilic layer 15 may also cover regions between the plurality of micro-reaction chambers 111 in the micro-chamber definition layer 11. Since the hydrophilic layer 15 is arranged on the surface of the micro-reaction chamber 111 (i.e., the side wall 111a and the bottom 111b), the hydrophilicity of the micro-reaction chamber 111 is improved, and the reaction system solution can automatically and gradually enter each micro-reaction chamber 111 based on capillary phenomenon in the absence of external driving force, thereby realizing automatic sample injection and sample filling.

For example, the material of the hydrophilic layer 15 is silicon oxide or silicon oxynitride after surface alkali treatment, and the silicon oxide is, for example, silicon dioxide ($SiO_2$). The surface alkali treatment refers to the soaking treatment of a portion of silicon oxide or silicon oxynitride covering the side wall 111a and the bottom 111b of the micro-reaction chamber 111 by using an alkali solution, so as to carry out surface modification to form the hydrophilic layer 15. For example, the alkali solution used for surface alkali treatment is potassium hydroxide (KOH) solution, and the mass fraction of the potassium hydroxide solution is about 0.4%. For example, the portion of the silicon oxide or silicon oxynitride covering the side wall 111a and the bottom 111b of the micro-reaction chamber 111 is soaked with the potassium hydroxide solution for about 15 minutes, and then cleaned, dried, etc., so that modification can be realized to form the hydrophilic layer 15. The operation method of surface alkali treatment is simple, the cost of reagents used is low, it is easy to obtain, and complex external equipment is not needed, which can improve the treatment efficiency.

It should be noted that, in the embodiment of the present disclosure, the alkali solution used for surface alkali treatment is not limited to potassium hydroxide solution, other suitable alkali solutions may also be used, and the concentration (e.g., mass fraction) of the alkali solution is not limited, which may be determined according to actual needs.

It should be noted that, in the embodiment of the present disclosure, the hydrophilic layer 15 may also be made of other suitable inorganic or organic materials, and the surface modification method may also adopt other suitable modification methods as long as the hydrophilicity of the hydrophilic layer 15 is ensured. For example, the hydrophilic layer 15 may be directly prepared by using a hydrophilic material. For another example, the hydrophilic layer 15 may be made of a material not having hydrophilicity. In this case, it is necessary to perform hydrophilic treatment to the surface of the hydrophilic layer 15 away from the micro-chamber definition layer 11, so that the surface of the hydrophilic layer 15 away from the micro-chamber definition layer 11 has hydrophilicity. For example, if a non-hydrophilic material, such as silicon nitride, is used, the hydrophilic treatment may be performed by means of, for example, gel modification method, ultraviolet radiation method, plasma method, etc. For example, the surface of the non-hydrophilic material may have hydrophilic groups to make it hydrophilic.

Figure 8A:
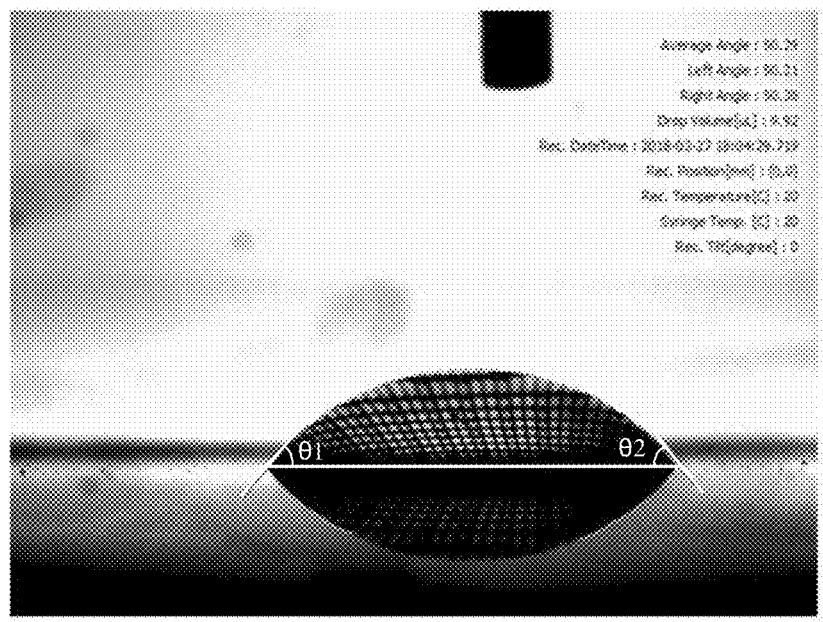
FIG. 8A is a schematic diagram of performing a surface hydrophilicity and hydrophobicity test on the micro-reaction chamber before surface modification provided by some embodiments of the present disclosure.
Figure 8B:
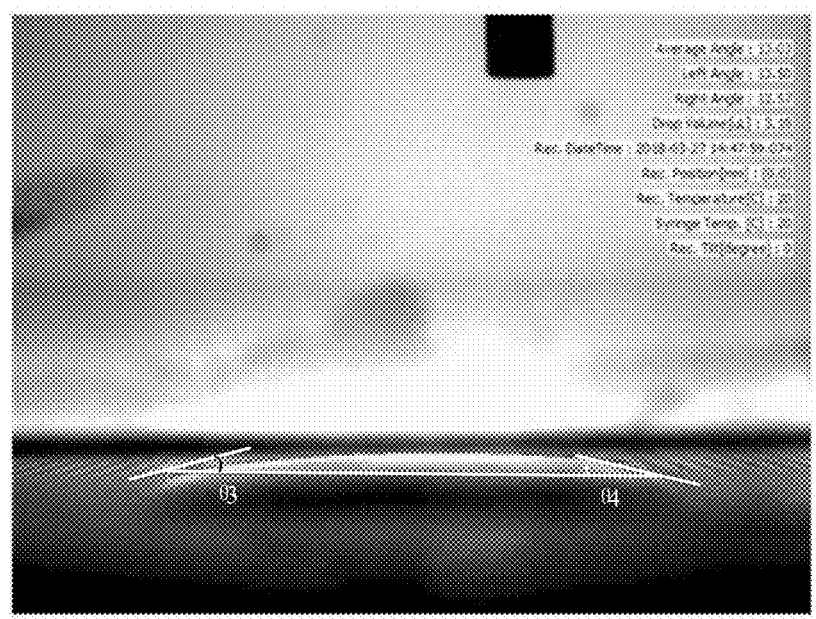
FIG. 8B is a schematic diagram of performing a surface hydrophilicity and hydrophobicity test on the micro-reaction chamber after surface modification provided by some embodiments of the present disclosure.

FIG. 8A is a schematic diagram of performing a surface hydrophilicity and hydrophobicity test on the micro-reaction chamber before surface modification provided by some embodiments of the present disclosure, and FIG. 8B is a schematic diagram of performing a surface hydrophilicity and hydrophobicity test on the micro-reaction chamber after surface modification provided by some embodiments of the present disclosure. Here, "micro-reaction chamber before surface modification" refers to the micro-reaction chamber when no hydrophilic layer is provided on the bottom and side wall of the micro-reaction chamber, and is hereinafter referred to as the first micro-reaction chamber; "micro-reaction chamber after surface modification" means the micro-reaction chamber when hydrophilic layer is provided on the bottom and side wall of the micro-reaction chamber, that is, the micro-reaction chamber 111 in the detection chip 100 provided by the embodiment of the present disclosure, which is hereinafter referred to as the second micro-reaction chamber.

For example, in the testing process shown in FIG. 8A and FIG. 8B, using deionized water as the test droplet, the contact angle of the droplet on the surface (bottom or side wall) of the micro reaction chamber is tested. As shown in FIG. 8A, the volume of the first test droplet is 9.92 L, and for the first micro-reaction chamber, the left contact angle θ1 between the first test droplet and the surface of the first micro-reaction chamber is about 50.21°, and the right contact angle θ2 between the first test droplet and the surface of the first micro-reaction chamber is about 50.38°, so that the average contact angle between the first test droplet and the surface of the first micro-reaction chamber is about 50.29°. As shown in FIG. 8B, for the second micro-reaction chamber, the volume of the second test droplet is 3.19 L, and the left contact angle θ3 between the second test droplet and the surface of the second micro-reaction chamber is about 13.50°, and the right contact angle θ4 between the second test droplet and the surface of the second micro-reaction chamber is about 12.57°, so that the average contact angle between the second test droplet and the surface of the second micro-reaction chamber is about 13.03°. It can be seen that in some embodiments of the present disclosure, since the hydrophilic layer 15 is provided on the surface of the micro-reaction chamber 111, the hydrophilicity is greatly improved, and the contact angle between the droplet and the surface of the micro-reaction chamber 111 is small.

For example, as shown in FIG. 3 and FIG. 4, the second insulation layer 16 is disposed between the heating electrode 12 and the micro-chamber definition layer 11. The second insulation layer 16 is used to protect the heating electrode 12 to provide insulation effect, prevent liquid from eroding the heating electrode 12, slow down the aging of the heating electrode 12, and play a planarization role. For example, the second insulation layer 16 may be made of an inorganic insulating material or an organic insulating material. For example, the material of the second insulation layer 16 is silicon dioxide or silicon nitride. For example, the material of the second insulation layer 16 may be the same as or different from the material of the first insulation layer 14.

For example, as shown in FIG. 2, the sample injection port 31 and the sample outlet port 32 are located on opposite sides of the plurality of micro-reaction chambers 111, for example, on both sides of the plurality of micro-reaction chambers 111 along the first direction. For example, the sample injection port 31 is a channel through which the reaction system solution may be injected, and the sample outlet port 32 is a channel through which the excess reaction system solution may be discharged or the sample stock solution may be separated. For example, the reaction system solution may be injected into the sample injection port 31 by a microinjection pump or a pipette, and then may enter each micro-reaction chamber 111 by self-priming liquid. The reaction system solution that has not entered the micro-reaction chamber 111 is discharged from the detection chip 100 through the sample outlet port 32. For example, the sample injection port 31 and the sample outlet port 32 are symmetrically distributed with respect to the central axis of the detection chip 100, so that the flow of the reaction system solution in the detection chip 100 is more uniform, and it is convenient for the reaction system solution to enter into each micro-reaction chamber 111.

Figure 9:
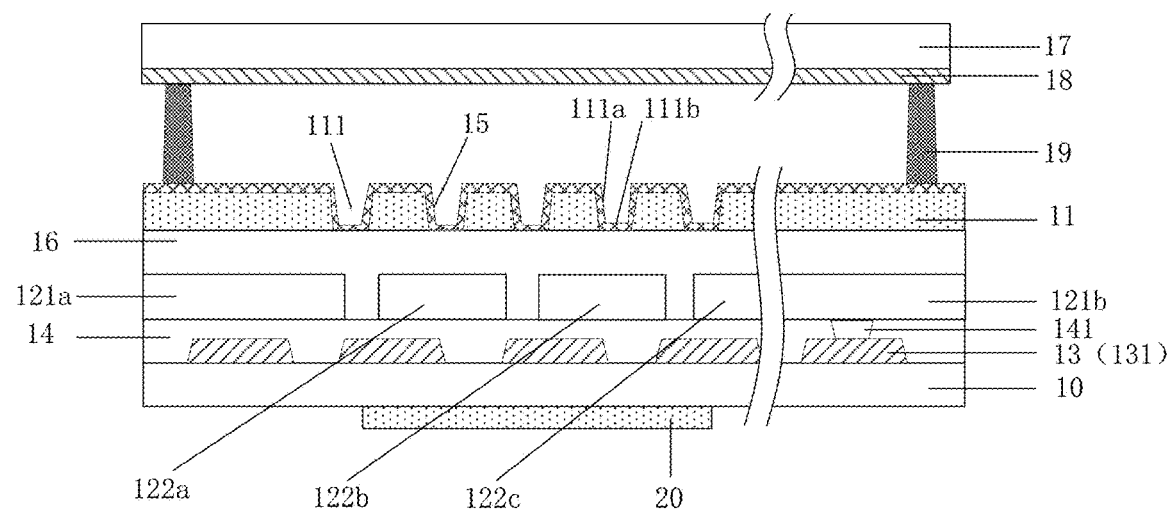
FIG. 9 is a schematic cross-sectional view of another detection chip provided by some embodiments of the present disclosure.

FIG. 9 is a schematic cross-sectional view of another detection chip provided by some embodiments of the present disclosure. For example, as shown in FIG. 9, except for further comprising a second substrate 17, a hydrophobic layer 18 and a bonding layer 19, the detection chip 100 provided by the embodiment is basically the same as the detection chip 100 shown in FIG. 2, FIG. 3 and FIG. 4.

In the embodiment, the second substrate 17 is opposite to the first substrate 10, and plays the roles of protection, support and isolation. A gap is provided between the second substrate 17 and the first substrate 10. For example, the second substrate 17 may be a glass substrate.

Since both the first substrate 10 and the second substrate 17 may be glass substrates, and the micro-chamber definition layer 11 may be made of photoresist, the detection chip 100 may be manufactured by using the micro-machining manner of glass-based semiconductor process, which is compatible with semiconductor production lines, simple in preparation and low in production cost, and is conducive to large-scale standardized production.

It should be noted that other suitable substrates may be used for the first substrate 10 and the second substrate 17 in the embodiment of the present disclosure, which is not limited by the embodiment of the present disclosure. For example, the shape of the first substrate 10 and the shape of the second substrate 17 may be rectangular or other suitable shapes, which is not limited by the embodiments of the present disclosure.

For example, the hydrophobic layer 18 covers a side of the second substrate 17 facing the first substrate 10. The hydrophobic layer 18 has hydrophobic and lipophilic characteristics, and by arranging the hydrophobic layer 18, the reaction system solution can easily enter each micro-reaction chamber 111. For example, the material of the hydrophobic layer 18 is silicon nitride modified by Plasma. Of course, the embodiments of the present disclosure are not limited to this, and the hydrophobic layer 18 may also be made of resin or other suitable inorganic or organic materials, as long as a side of the hydrophobic layer 18 facing the micro-chamber definition layer 11 is ensured to have hydrophobicity. For example, the hydrophobic layer 18 may be directly prepared using hydrophobic materials. For another example, the hydrophobic layer 18 may be made of a material without hydrophobicity, in this case, the surface of the hydrophobic layer 18 facing the micro-chamber definition layer 11 needs to be performed hydrophobic treating, so that the hydrophobic layer 18 has hydrophobicity.

In the embodiment of the present disclosure, the hydrophilic layer 15 and the hydrophobic layer 18 may jointly adjust the surface contact angle of the droplet of the reaction system solution, so that the detection chip 100 can realize self-priming liquid sample injection and oil sealing. For example, in the detection chip 100, the hydrophobic property of the outside of the micro-reaction chamber 111 is improved by the hydrophobic layer 18, and the hydrophilicity of the inside surface of the micro-reaction chamber 111 is good, so that the reaction system solution infiltrates from the outside of the micro-reaction chamber 111 to the inside of the micro-reaction chamber 111. Therefore, under the joint action of the hydrophilic layer 15 and the hydrophobic layer 18, the reaction system solution can easily enter each micro-reaction chamber 111.

For example, the sample injection port 31 and the sample outlet port 32 both penetrate through the second substrate 17 and the hydrophobic layer 18 (not shown in FIG. 9), thereby facilitating the flow of liquid into and out of the detection chip 100. For example, the sample injection port 31 and the sample outlet port 32 may be formed by laser drilling.

For example, the bonding layer 19 is located between the first substrate 10 and the second substrate 17, for example, located at the edge of the detection chip 100. The bonding layer 19 may connect the first substrate 10 and the second substrate 17 to each other to form a cell, and may maintain a distance between the first substrate 10 and the second substrate 17. For example, the material of the bonding layer 19 is thermosetting adhesive or photosensitive adhesive containing a spacer. For example, when thermosetting adhesive is used, a thickness of the film layer formed by thermosetting adhesive is 50-500 microns; when the photosensitive adhesive containing the spacer is used, a size of the spacer is 50-500 microns (when the spacer is spherical, a diameter of the spacer is 50-500 microns). For example, the photosensitive adhesive may be an ultraviolet (UV) curable acrylic resin. The shape of the spacer may be spherical, columnar or ellipsoidal. In this case, the spacer may be uniformly mixed in the photosensitive adhesive, and then the first substrate 10 and the second substrate 17 may be cell-assembled by curing and packaging.

For example, the space surrounded by the bonding layer 19, the second substrate 17 and the micro-chamber definition layer 11 is an accommodation chamber. For example, by designing the distribution position and shape of the bonding layer 19, the first substrate 10 and the second substrate 17 may be cell-assembled, while an accommodation chamber with a desired shape may be formed. The top surface of the accommodation chamber is defined by the second substrate 17, the bottom surface of the accommodation chamber is defined by the micro-chamber definition layer 11, and the side surface of the accommodation chamber is defined by the bonding layer 19. For example, the accommodation chamber is an empty chamber in the detection chip 100. During the use of the detection chip 100, the accommodation chamber is filled with a continuous phase (e.g., mineral oil), and the reaction system solution enters each micro-reaction chamber 111 as a dispersed phase. The accommodation chamber will be described in detail later, which will not be described here.

For example, any suitable process may be used to prepare the bonding layer 19, so that the first substrate 10 and the second substrate 17 may be cell-assembled with each other to form an accommodation chamber with a desired shape.

For example, in some examples, the preparation process of the bonding layer 19 is as follows. The UV adhesive doped with a spacer (e.g., having a diameter of 100 microns) is placed in a dispenser. After parameters such as the package shape, dispensing speed etc., are set, dispensing may be performed on the first substrate 10 (at this time, various film layers, such as the control circuit layer 13, the heating electrode 12 and the micro-chamber definition layer 11, are already formed on the first substrate 10, which are not listed here). After dispensing, the second substrate 17 is moved by the suction cup (at this time, the hydrophobic layer 18 is formed on the second substrate 17). After alignment, the first substrate 10 and the second substrate 17 are attached, and then ultraviolet light is immediately irradiated to cure the UV adhesive.

For example, in other examples, the preparation process of the bonding layer 19 is as follows. Die-cutting or laser cutting the thermosetting adhesive film material with a thickness of about 100 microns according to the required shape (such as the shape of the accommodation chamber). After removing the hard release film, the thermosetting adhesive film is attached to the second substrate 17 (at this time, the hydrophobic layer 18 has been formed on the second substrate 17) by a jig. The thermosetting adhesive film is heated to 120° C. to make the thermosetting adhesive film sticky to bond with the second substrate 17. After cooling, taking out and removing the soft release film, the thermosetting adhesive film is aligned with the first substrate 10 (at this time, various film layers, such as the control circuit layer 13, the heating electrode 12 and the micro-chamber definition layer 11, are formed on the first substrate 10, which are not listed here), and the heating process is repeated, so that the first substrate 10 and the second substrate 17 are cell-assembled to each other through the thermosetting adhesive film.

For example, in some examples, as shown in FIG. 9, the detection chip 100 may further include a temperature sensor 20. The temperature sensor 20 is disposed on a side of the first substrate 10 away from the micro-chamber definition layer 11, and is configured to sense the temperature of the reaction region 21 of the detection chip 100, thereby realizing a more accurate temperature control process. The temperature sensor 20 may be any type of temperature sensor, which is not limited by the embodiments of the present disclosure. Of course, the temperature sensor 20 may also be omitted from the detection chip 100, and the temperature sensor may be provided by the corresponding control device or installation device when in use, which may be determined according to actual requirements, and the embodiment of the present disclosure is not limited to this.

Figure 10:
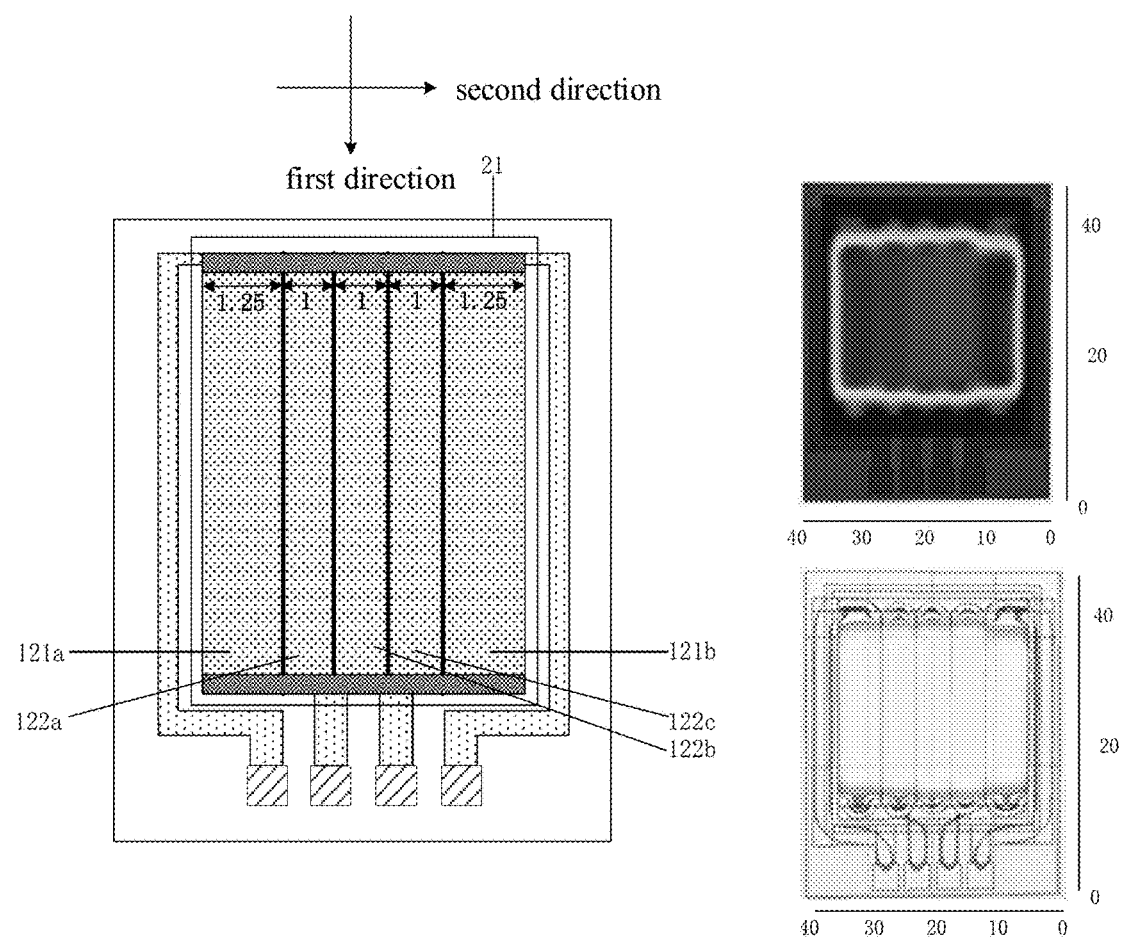
FIG. 10 is a thermal effect simulation diagram of a detection chip provided by some embodiments of the present disclosure.

FIG. 10 is a thermal effect simulation diagram of a detection chip provided by some embodiments of the present disclosure. For example, the detection chip 100 is the detection chip shown in FIG. 2, and a width ratio of the first sub-electrode to the second sub-electrode is 1.25:1. According to FIG. 10, the temperature in the reaction region 21 of the detection chip 100 is not only uniformly distributed along the first direction, but also uniformly distributed along the second direction. The temperature uniformity in the reaction region 21 of the detection chip 100 is good, which can realize highly efficient, accurate and uniform temperature control, thereby reducing the area of the edge low-temperature region, effectively reducing the chip size and increasing the number of micro-reaction chambers.

Figure 11:
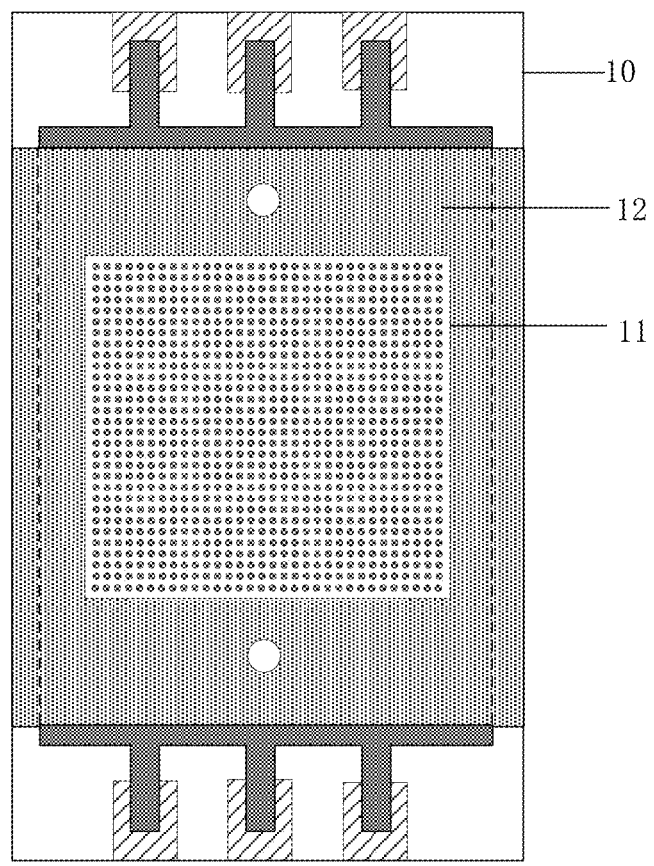
FIG. 11 is a schematic plan view of a detection chip provided by some embodiments of the present disclosure.
Figure 12A:
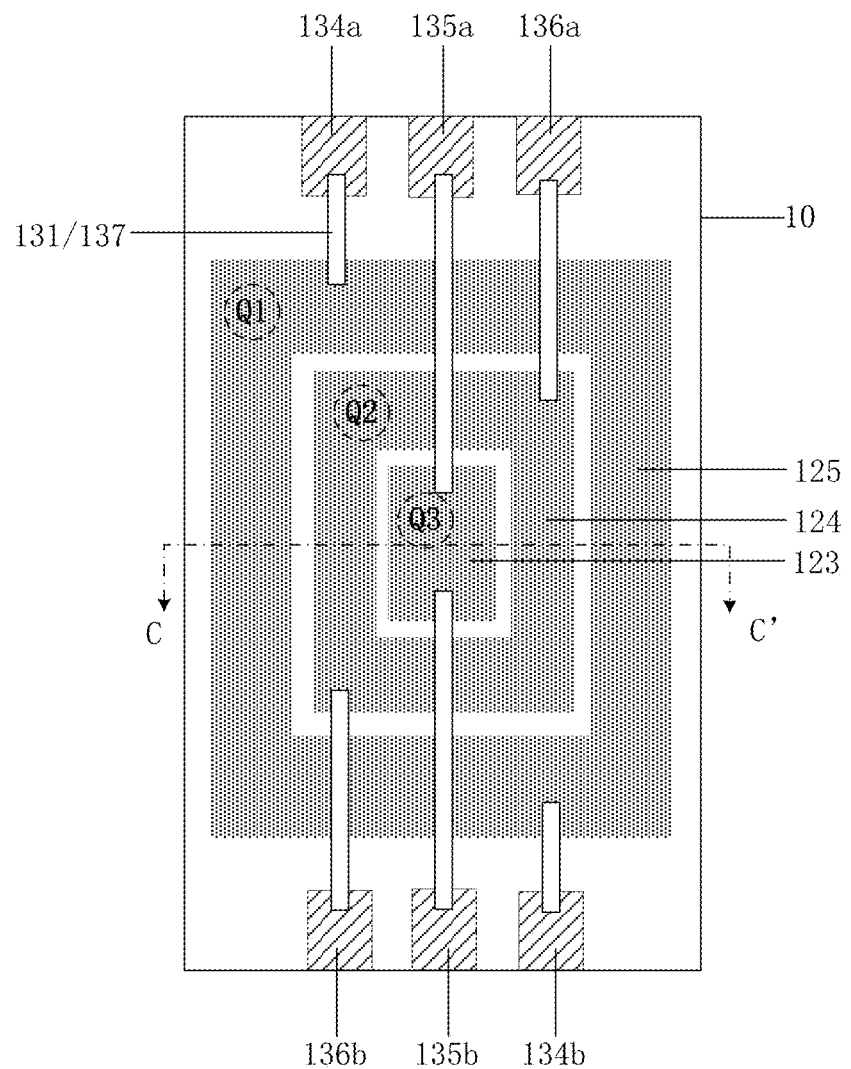
FIG. 12A is a schematic plan view of the heating electrode of the detection chip shown in FIG. 11.

FIG. 11 is a schematic plan view of a detection chip provided by some embodiments of the present disclosure, and FIG. 12A is a schematic plan view of a heating electrode of the detection chip shown in FIG. 11. For example, as shown in FIG. 11 and FIG. 12A, except for the arrangement manner of the heating electrode 12 and the connection electrode, the detection chip 100 provided by the embodiment is basically the same as the detection chip 100 shown in FIGS. 2-4.

For example, in the embodiment, the heating electrode 12 includes a plurality of sub-electrodes, such as sub-electrodes 123, 124, 125. The orthographic projections of a plurality of sub-electrodes 123, 124 and 125 on the first substrate 10 are sequentially surrounded. The orthographic projection of the sub-electrode except the sub-electrode located at the center of the heating electrode 12 is annular. That is, the orthographic projection of sub-electrode 124 surrounds the orthographic projection of sub-electrode 123 and the orthographic projection of sub-electrode 125 surrounds the orthographic projection of sub-electrode 124. Except for the sub-electrode 123 located at the center of the heating electrode 12, the orthographic projections of other sub-electrodes (i.e., sub-electrodes 124 and 125) are annular. The orthographic projection of the sub-electrode 123 is a solid pattern. For example, the orthographic projections of the sub-electrodes 123, 124, 125 may have a gap between them, which is greater than 25 microns. It should be noted that the size of the gap may be determined according to actual requirements, for example, the size of the gap may also be 0, that is, there may be no gap between the orthographic projections of the sub-electrodes 123, 124 and 125, which is not limited by the embodiment of the present disclosure.

For example, the plurality of sub-electrodes 123, 124, 125 are insulated from each other. For example, the sub-electrodes 123, 124, and 125 may be disposed in different layers so as to be insulated from each other. For example, the sub-electrodes 123, 124, and 125 may be arranged on the same layer with a certain gap, so that they are insulated from each other.

Since the plurality of sub-electrodes 123, 124, 125 are insulated from each other, different electrical signals may be supplied to the sub-electrodes 123, 124, 125, respectively, so that the heating values per unit time of the sub-electrodes 123, 124, 125 are different. For example, in some examples, the electrical signal provided to the sub-electrode 125 is relatively large (e.g., the voltage value is relatively high), so that the sub-electrode 125 can release more heat, and the heating value per unit time of the sub-electrode 125 is relatively large, thereby reducing the edge heat dissipation effect and increasing the edge temperature of the heating electrode 12. The electric signal supplied to the sub-electrode 123 is small (for example, the voltage value is low), so that the sub-electrode 123 can release less heat, and the heating value per unit time of the sub-electrode 123 is small, and the center temperature of the heating electrode 12 is not too high. For example, the magnitude of the electrical signal supplied to the sub-electrode 124 is between the above two.

Therefore, the detection chip 100 provided by the embodiment of the present disclosure can realize high-efficiency, accurate and uniform temperature control, improve temperature uniformity, and solve the problems of high center temperature and low edge temperature of a conventional detection chip, thereby reducing the area of the edge low-temperature region, effectively reducing chip size and increasing the number of micro-reaction chambers. In addition, the detection chip 100 provided by the embodiment of the present disclosure can enable the plurality of micro-reaction chambers 111 to receive uniform heat, which not only helps to improve the efficiency of amplification reaction in the detection chip 100, but also helps to improve the accuracy of the detection result. The detection chip 100 can detect nucleic acid molecules extracted from body fluids such as blood and urine more simply, sensitively and non-invasively, and realize auxiliary diagnosis and treatment in the fields of single cell analysis, early cancer diagnosis and prenatal diagnosis.

Figure 12B:
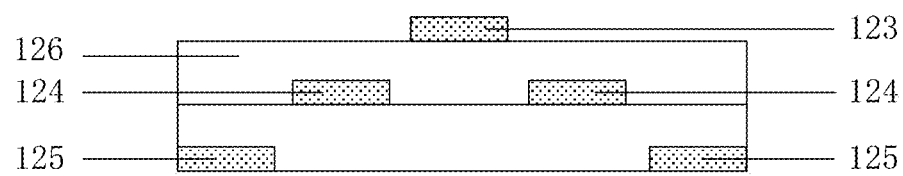
FIG. 12B is a schematic cross-sectional view of the heating electrode shown in FIG. 12A along C-C'.

FIG. 12B is a schematic cross-sectional view of the heating electrode shown in FIG. 12A along C-C'. It should be noted that only the cross section of the heating electrode 12 is shown in FIG. 12B, and other structures in the detection chip 100 are not shown in FIG. 12B.

For example, as shown in FIG. 12B, in some examples, a plurality of sub-electrodes 123, 124, 125 are located in different layers. For example, the sub-electrodes 123, 124, and 125 are respectively located in three different film layers. Interlayer insulation layers 126 are provided between the sub-electrode 123 and the sub-electrode 124, and between the sub-electrode 124 and the sub-electrode 125. The interlayer insulation layers 126 keep the sub-electrodes 123, 124 and 125 insulated from each other. For example, the interlayer insulation layer 126 may be made of an inorganic insulating material or an organic insulating material.

In the example, the heating electrode 12 is a multilayer structure, and for example, a multi-layer ITO film may be formed by sputtering, etching, deposition, etc., so as to obtain the heating electrode 12 with sub-electrodes 123, 124, 125. Since the sub-electrodes 123, 124 and 125 are located in different layers and are insulated from each other by the interlayer insulation layer 126, the orthographic projections of the sub-electrodes 123, 124, and 125 on the first substrate 10 may not have gaps with each other, thereby reducing the process difficulty.

It should be noted that in the embodiment of the present disclosure, a plurality of sub-electrodes may be located in different layers or in the same layer, which may be determined according to actual needs, and the embodiment of the present disclosure is not limited to this. For example, in other examples, the sub-electrodes 123, 124, and 125 may be located in the same layer, and the sub-electrodes 123, 124, and 125 are insulated from each other by setting gaps. At this time, the heating electrode 12 has a single-layer structure, which can reduce the thickness of the chip and make the chip lighter and thinner. For example, when the sub-electrodes 123, 124, and 125 are located in different layers, the specific film layer order is not limited.

Figure 12C:
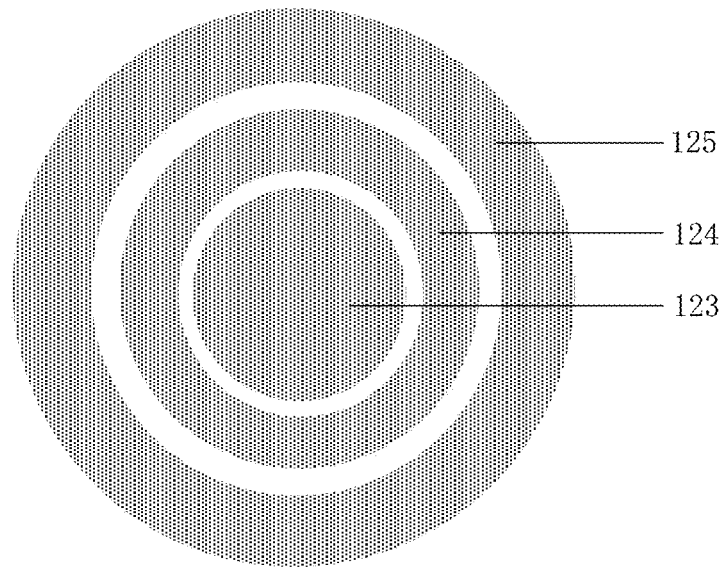
FIG. 12C is a schematic plan view of a heating electrode of another detection chip provided by some embodiments of the present disclosure.

For example, a cross section of at least one of the plurality of sub-electrodes is in a square ring shape, a circular ring shape or an elliptical ring shape, and the cross section is parallel to the first substrate 10. For example, in some examples, as shown in FIG. 12A, the cross section shape of the sub-electrodes 124 and 125 is a square ring shape, and accordingly, the cross section shape of the sub-electrode 123 is rectangular or square. For example, in other examples, as shown in FIG. 12C, the cross section shape of the sub-electrodes 124 and 125 are circular-ring-shaped, and accordingly, the cross section shape of the sub-electrode 123 is circular.

For example, the cross-sectional shape of the sub-electrode may be matched with a shape of an array formed by a plurality of micro-reaction chambers 111, so as to improve the temperature uniformity of the region where the micro-reaction chambers 111 are located. For example, when the heating electrode 12 adopts the shape shown in FIG. 12A, a plurality of micro-reaction chambers 111 may form a rectangular array; when the heating electrode 12 adopts the shape shown in FIG. 12C, a plurality of micro-reaction chambers 111 may form a circular array.

It should be noted that, in the embodiment, the number of sub-electrodes may be determined according to actual needs, for example, 2, 3, 4 or other numbers, as long as the number of sub-electrodes is greater than or equal to 2, which is not limited by the embodiment of the present disclosure.

For example, as shown in FIG. 11 and FIG. 12A, in the detection chip 100, the control circuit layer 13 includes a plurality of connection electrodes, such as connection electrodes 134a, 134b, 135a, 135b, 136a and 136b. These connection electrodes are divided into a plurality of groups. For example, the connection electrodes 134a and 134b are the first group, the connection electrodes 135a and 135b are the second group, and the connection electrodes 136a and 136b are the third group, and each group of connection electrodes includes two connection electrodes.

A plurality of groups of connection electrodes correspond to a plurality of sub-electrodes in a one-to-one correspondence relationship, and each group of connection electrodes is configured to transmit an electrical signal to the corresponding sub-electrode through the control circuit 131. For example, the number of groups of connection electrodes is equal to the number of sub-electrodes. For example, the first group of connection electrodes 134a and 134b correspond to the sub-electrode 125, and are configured to transmit a first electrical signal to the sub-electrodes 125 through the control circuit 131; the second group of connection electrodes 135a and 135b correspond to the sub-electrode 123, and are configured to transmit the second electrical signal to the sub-electrode 123 through the control circuit 131; the third group of connection electrodes 136a, 136b correspond to the sub-electrode 124, and are configured to transmit a third electrical signal to the sub-electrode 124 through the control circuit 131. It should be noted that the wire 137 in the control circuit 131 is used to represent the electrical connection relationship between the connection electrode and the corresponding sub-electrode, which is only schematic, but does not represent the actual connection structure between the connection electrode and the corresponding sub-electrode.

For example, the electrical signals transmitted by the plurality of connection electrodes are different from each other. That is, the first electrical signal, the second electrical signal and the third electrical signal are different from each other. For example, by providing a first electrical signal, a second electrical signal and a third electrical signal which are independent of each other to a plurality of groups of connection electrodes, the heating power of each sub-electrode may be independently controlled, so that the heating value per unit time of each sub-electrode is different. For example, in some examples, the first electrical signal is relatively large (e.g., the voltage value is relatively high), so that the sub-electrode 125 can release more heat, and the heating value per unit time of the sub-electrode 125 is relatively large, so as to reduce the edge heat dissipation effect, thereby increasing the edge temperature of the heating electrode 12. For example, the second electrical signal is small (e.g., the voltage value is relatively low), so that the sub-electrode 123 can release less heat, and the heating value per unit time of the sub-electrode 123 is small, so that the center temperature of the heating electrode 12 is not too high. For example, the third electrical signal is smaller than the first electrical signal and larger than the second electrical signal.

It should be noted that the electrical signals transmitted by the plurality of groups of connection electrodes are different from each other, which means that the electrical signals transmitted by the plurality of groups of connection electrodes are not the same signal, that is, these electrical signals are different at at least one time point, but not at every time point. For example, at some time points, the electrical signals transmitted by the plurality of groups of connection electrodes may be the same. For example, at the initial time point of using the detection chip 100, the electrical signals transmitted by the plurality of groups of connection electrodes may be the same, and at this time, the electrical signals are larger, so that the detection chip 100 can be heated up rapidly.

For example, for the connection electrodes in the same group, the two connection electrodes are located on opposite sides of the detection chip 100. For example, the connection electrode 134a in the first group of connection electrodes, the connection electrode 135a in the second group and the connection electrode 136a in the third group are located on one side of the detection chip 100, while the connection electrode 134b in the first group, the connection electrode 135b in the second group and the connection electrode 136b are located on the other side of the detection chip 100. Therefore, a uniform current can be generated in each sub-electrode.

It should be noted that the number of connection electrodes in each group of connection electrodes is not limited, and may be 2, 3, 4 or any other number, which may be determined according to actual requirements. Arrangement locations of the connection electrodes in each group of connection electrodes is not limited, which may be determined according to actual requirements.

For example, when using the detection chip 100, a temperature measuring device (such as an infrared thermometer) is used to monitor the front image of the detection chip 100 in real time to obtain real-time temperature information. For example, as shown in FIG. 12A, the temperature information T1 at number Q1, the temperature information T2 at number Q2 and the temperature information T3 at number Q3 are detected and stored, and the temperature information T1, T2 and T3 respectively reflect the real-time temperatures of the sub-electrodes 125, 124 and 123. Then, according to the difference between the temperature information T1, T2, T3 and the first target temperature, the signal powers respectively supplied to the first group of connection electrodes 134a and 134b, the third group of connection electrodes 136a and 136b, and the second group of connection electrodes 135a and 135b are determined by using PID (Proportional Integral Differential) algorithm. Detection-calculation is performed for a plurality of cycles, until each temperature reaches the first target temperature. Then, each temperature is maintained until the first-stage reaction in the detection chip 100 ends.

When the temperature of the detection chip 100 needs to drop to the second target temperature, the power supply is turned off, and a separately provided cooling unit (such as a fan) is started to blow and cool the back of the detection chip 100, while the infrared thermometer continues to monitor and acquire real-time temperature information. When the temperature of the detection chip 100 drops to near the second target temperature, according to the difference between the temperature information T1, T2, T3 and the second target temperature, the signal powers respectively supplied to the first group of connection electrodes 134a and 134b, the third group of connection electrodes 136a and 136b and the second group of connection electrodes 135a and 135b are determined by using the PID algorithm. Then, each temperature is maintained until the second-stage reaction in the detection chip 100 ends.

It should be noted that other structures and components in the detection chip 100 in the embodiment may refer to the detection chip 100 shown in FIG. 2-FIG. 4, and similar structures are not repeated here.

Figure 13A:
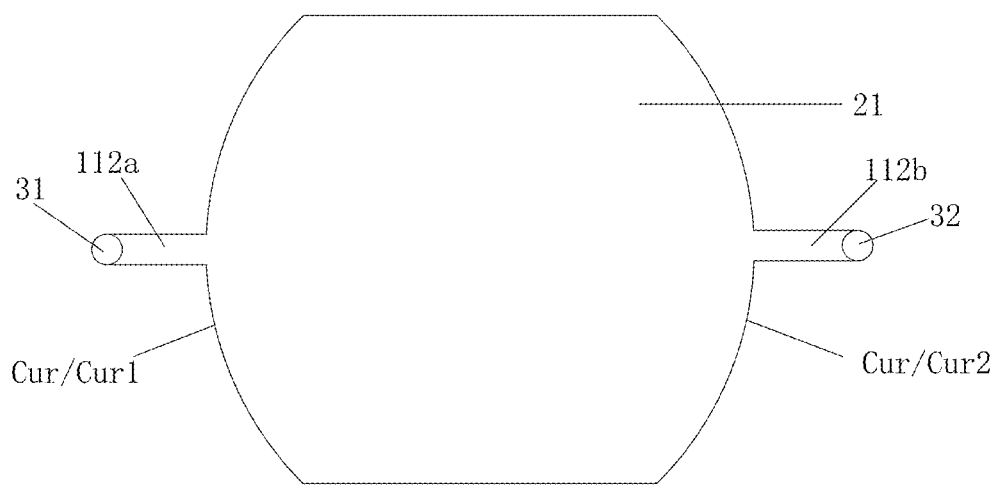
FIG. 13A is a top view of an accommodation chamber of a detection chip provided by some embodiments of the present disclosure.
Figure 13B:
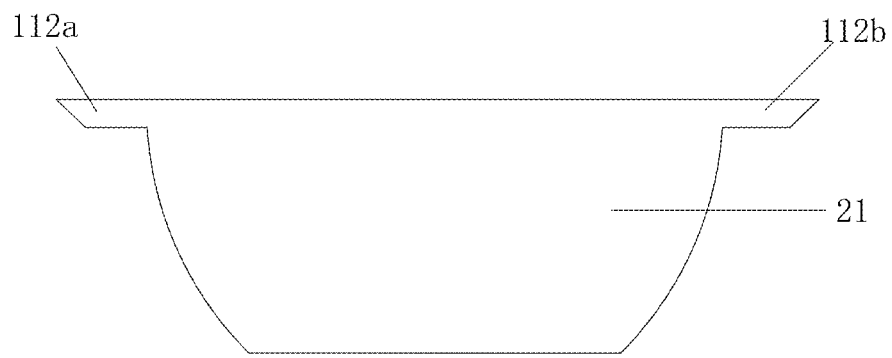
FIG. 13B is a front view of an accommodation chamber of a detection chip provided by some embodiments of the present disclosure.

FIG. 13A is a top view of an accommodation chamber of a detection chip provided by some embodiments of the present disclosure, and FIG. 13B is a front view of an accommodation chamber of a detection chip provided by some embodiments of the present disclosure. It should be noted that since the accommodation chamber is an empty chamber in the detection chip, in order to reflect the shape of the accommodation chamber, other structures surrounding the accommodation chamber in the detection chip are omitted in FIG. 13A and FIG. 13B, and the outline of the accommodation chamber is mainly shown.

For example, in some embodiments, as shown in FIG. 13A and FIG. 13B, the detection chip 100 further includes an accommodation chamber 21. For example, the accommodation chamber 21 is an empty chamber in the detection chip 100, and a plurality of micro-reaction chambers 111 are located in the accommodation chamber 21. During the use of the detection chip 100, the accommodation chamber 21 is filled with liquid, such as continuous phase (such as mineral oil), and the reaction system solution enters each micro-reaction chamber 111 as dispersed phase. For example, the accommodation chamber 21 is a space surrounded by the bonding layer 19, the second substrate 17 and the micro-chamber definition layer 11. For example, the bonding layer 19 surrounds the periphery of an array formed by a plurality of micro-reaction chambers 111, so that the plurality of micro-reaction chambers 111 are located in the accommodation chamber 21.

For example, the micro-chamber definition layer 11 also defines a sample injection channel 112a and a sample outlet channel 112b, the sample injection channel 112a and the sample outlet channel 112b both are communicated with the accommodation chamber 21. For example, the sample injection channel 112a also is communicated with the sample injection port 31, so that liquid can flow from the sample injection port 31 into the accommodation chamber 21 through the sample injection channel 112a. For example, the sample outlet channel 112b also is communicated with the sample outlet port 32, so that liquid can flow out of the detection chip 100 from the accommodation chamber 21 through the sample outlet channel 112b and the sample outlet port 32. For example, the sample injection channel 112a and the sample outlet channel 112b may have any shape such as a straight line, a broken line or a curve line, which may be determined according to actual requirements, and the embodiment of the present disclosure is not limited to this. For example, a length of the sample injection channel 112a is 1000-10000 microns, and a length of the sample outlet channel 112b is 1000-10000 microns, the length of the sample injection channel 112a may be equal to or different from the length of the sample outlet channel 112b. It should be noted that in other examples, the sample injection port 31 and the sample outlet port 32 may be directly arranged on the boundary of the accommodation chamber 21 and the sample injection port 112a and the sample outlet port 112b may be omitted.

As shown in FIG. 13A and FIG. 13B, for example, the accommodation chamber 21 has an arc boundary Cur, the arc boundary Cur is a curved surface, and the trajectory of the curved surface in a plane parallel to the first substrate 10 is a curve, and the trajectory of the curved surface in a plane perpendicular to the first substrate 10 is also a curve. For example, the arc boundary Cur includes a first arc boundary Cur1 and a second arc boundary Cur2. The first arc boundary Cur1 and the second arc boundary Cur2 are located at opposite sides of the accommodation chamber 21. For example, the arc boundary Cur of the accommodation chamber 21 is located at joints of the accommodation chamber 21 and the sample injection channel 112a, and the accommodation chamber 21 and the sample outlet channel 112b. In this example, for example, the sample injection channel 112a and the sample outlet channel 112b are located on opposite sides of the accommodation chamber 21, the sample injection channel 112a is communicated with the accommodation chamber 21 at the first arc boundary Cur1, and the sample outlet channel 112b is communicated with the accommodation chamber 21 at the second arc boundary Cur2.

For example, a radian of the arc boundary Cur is less than or equal to $\pi/2$, that is, a central angle corresponding to the arc boundary Cur is less than or equal to 90°. For example, the radian of the first arc boundary Cur1 and the radian of the second arc boundary Cur2 are both less than or equal to $\pi/2$, and the radian of the first arc boundary Cur1 and the radian of the second arc boundary Cur2 may be equal or unequal.

It should be noted that in the embodiment of the present disclosure, the arc boundary Cur is a curved surface, the trajectory of the curved surface may be a curve only in a plane parallel to the first substrate 10, or the trajectory of the curved surface may be a curve only in a plane perpendicular to the first substrate 10, or the trajectory of the curved surface may be a curve both in a plane perpendicular to the first substrate 10 and in a plane parallel to the first substrate 10, the embodiments of the present disclosure are not limited to this.

In the detection chip 100 provided by the embodiment of the present disclosure, by setting the arc boundary Cur, uniform sample injection can be realized, which can effectively prevent air from entering the accommodation chamber 21 to generate bubbles, and reduce or avoid residual gas, thereby reducing or avoiding interference of bubbles on detection results.

Figure 14:
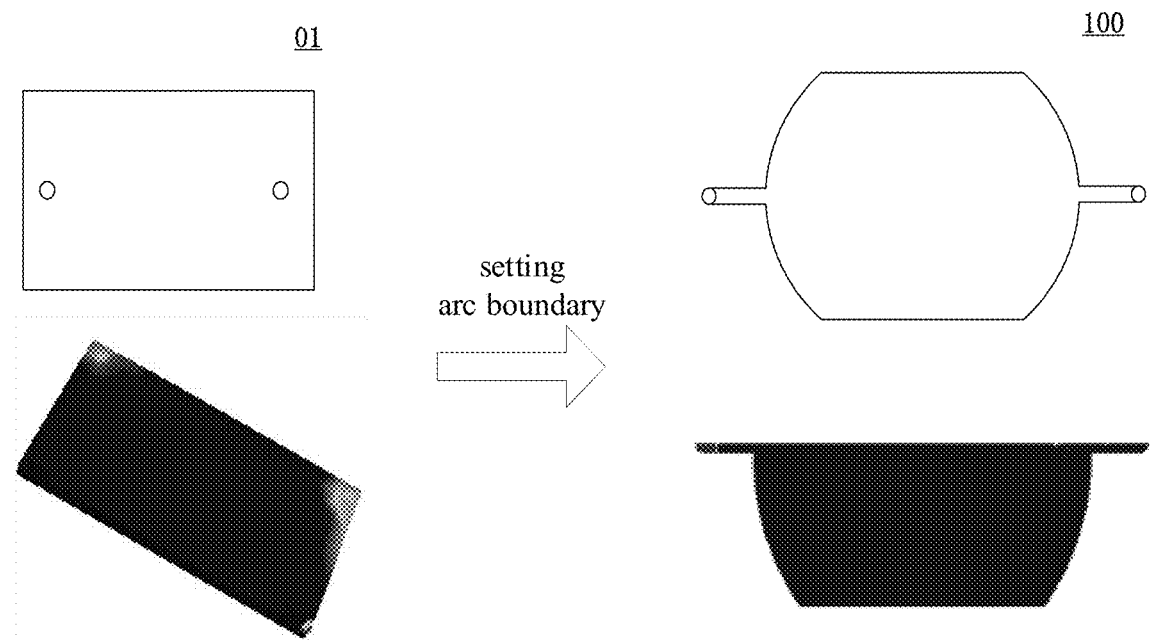
FIG. 14 is a simulation comparison diagram of air residual quantity of the detection chip provided by some embodiments of the present disclosure.

FIG. 14 is a simulation comparison diagram of air residual quantity of the detection chip provided by some embodiments of the present disclosure. As shown in FIG. 14, in a common detection chip 01, the accommodation chamber is generally cubic, that is, the accommodation chamber has no arc boundary. After the liquid is injected, bubbles are easily generated in the accommodation chamber of the detection chip 01, for example, the air residual quantity is 1.71%. For example, these bubbles may gather at the corners of the accommodation chamber, which will interfere with the detection results. However, in the detection chip 100 provided by the embodiment of the present disclosure, since the accommodation chamber 21 is set to have an arc boundary Cur, it is possible to avoid the generation of bubbles, for example, the air residual quantity is 0. Therefore, the detection chip 100 provided by the embodiment of the present disclosure can effectively prevent air from entering the accommodation chamber 21, reduce or avoid residual gas, thereby reducing or avoiding the interference of bubbles on the detection results.

It should be noted that, in the embodiment of the present disclosure, the detection chip 100 may also include more or less components, which are not limited to the components described above and may be determined according to actual needs, and the embodiment of the present disclosure is not limited to this.

The following is an exemplary description of the preparation process flow of the detection chip 100 provided by some embodiments of the present disclosure. For example, the detection chip 100 is prepared by sputter, plasma enhanced chemical vapor deposition (PECVD), Reactive Ion Etching (ME etch), photolithography and other processes in the semiconductor production line.

First, cleaning the first substrate 10 (for example, a glass substrate). For example, a thickness of the first substrate 10 is 500 microns. Then, depositing a metal material on the first substrate 10 at 240° C., to form the control circuit layer 13. For example, a material of the control circuit layer 13 is a laminated structure of Mo—Nd—Al alloy-Mo (Mo—AlNd—Mo), and the thickness of each single layer is 200 Å, 3000 Å and 800 Å, respectively.

Then, depositing a first insulation layer 14 at 200° C., and the material of the first insulation layer 14 is silicon dioxide with a thickness of 3000 Å or 4000 Å. Then, forming a through hole 141 in the first insulation layer 14 by means of etching process. For example, in this etching process, the process parameters may be set as follows: 150 mt/800 w/400,$O_2$/10 s; 60 mt/800 w/200,$CF_4$/50, $O_2$/2005; 130 mt/800 w/400,$O_2$/40 $CF_4$/30 s; 60 mt/800 w/200,$CF_4$/50 $O_2$/160 s.

Next, forming the heating electrode 12 by depositing. The material of the heating electrode 12 is ITO, and the thickness may be 560 Å, 900 Å or 1800 Å. It should be noted that the heating electrode 12 is, for example, the heating electrode shown in FIG. 2, and the heating electrode includes a plurality of sub-electrodes, for example, a first sub-electrode and a second sub-electrode, the width of the second sub-electrode is smaller than that of the first sub-electrode, so that the resistance value of the second sub-electrode is larger than that of the first sub-electrode. For example, in other examples, the heating electrode 12 shown in FIG. 12A may also be formed by a similar process.

Then, depositing to form a second insulating layer 16. The material of the second insulation layer 16 is silicon nitride with a thickness of 3000 Å or 4000 Å. Alternatively, the second insulation layer 16 may have a laminated structure of silicon dioxide and silicon nitride, with the thickness of silicon dioxide being 1000 Å, and the thickness of silicon nitride being 2000 Å.

Then, forming a micro-chamber definition layer 11. The PS adhesive is coated by spin coating process with process parameters of 30 Kpa\300 rpm*10 s, and then performing pre-baking for 120 s at 90° C. Repeating the steps of spin coating and pre-baking twice, exposing and developing for 100 s, and then performing post-baking at 230° C. for 30 minutes. Thereby, the micro-chamber definition layer 11 having a plurality of micro-reaction chambers 111 may be formed.

Then, forming a hydrophilic layer 15. Depositing a silicon dioxide layer at 200° C. with a thickness of 3000 Å. Coating PR adhesive, performing aligning and exposing, and developing to expose the micro-reaction chamber 111. The exposed micro-reaction chamber 111 is soaked with potassium hydroxide (KOH) solution with a mass fraction of about 0.4% for about 15 minutes, so that the silicon dioxide covering the side wall 111a and the bottom 111b of the micro-reaction chamber 111 is modified to obtain the hydrophilic layer 15.

Then, forming a hydrophobic layer 18 on the second substrate 17. Spin coating silicon nitride with a process parameter of 300 rpm*10 s, performing pre-baking at 90° C. for 120 s, and performing post-baking at 230° C. for 30 minutes. A surface modification treatment is performed by using a plasma modification method to modify silicon nitride, thereby forming a hydrophobic layer 18.

Finally, bonding the second substrate 17 and the first substrate 10 together by a bonding process, and the second substrate 17 and the first substrate 10 are cell-assembled to form a structure with an accommodation chamber 21, thereby obtaining the detection chip 100. For example, the second substrate 17 and the first substrate 10 may be bonded by using thermosetting adhesive or photosensitive adhesive containing a spacer. For the specific bonding method, please refer to the previous contents, which will not be repeated here.

It should be noted that, in the embodiment of this disclosure, the preparation process flow of the detection chip 100 described above may also include more steps and operations, and the execution order of each step is not limited, which may be determined according to actual requirements.

At least one embodiment of the disclosure also provides a reaction system, which comprises a control device and the detection chip according to any embodiment of the disclosure. The reaction system can realize high-efficiency, accurate and uniform temperature control, improve temperature uniformity, reduce an area of the edge low-temperature region of the detection chip, effectively reduce the chip size, increase the number of micro-reaction chambers, make the detection chip compatible with the semiconductor production line, and can realize large-scale standardized production. The reaction system provided by at least some embodiments can also realize uniform sample injection and reduce or avoid residual gas, thereby reducing or avoiding the interference of bubbles on the detection results.

Figure 15:
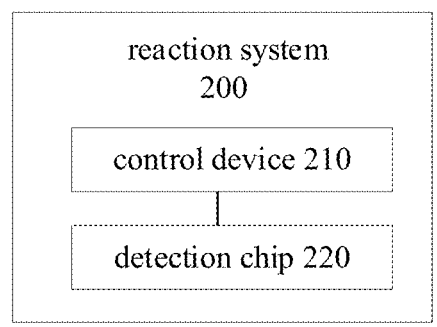
FIG. 15 is a schematic block diagram of a reaction system provided by some embodiments of the present disclosure.

FIG. 15 is a schematic block diagram of a reaction system provided by some embodiments of the present disclosure. For example, as shown in FIG. 15, the reaction system 200 includes a control device 210 and a detection chip 220. The control device 210 is electrically connected with the detection chip 220, and is configured to apply an electrical signal to the detection chip 220. For example, the detection chip 220 is a detection chip provided by any embodiment of the present disclosure, such as the above-mentioned detection chip 100. For example, a plurality of micro-reaction chambers of the detection chip 220 may contain reaction system solution. The control device 210 applies an electrical signal to the connection electrode of the detection chip 220, and the electrical signal is transmitted to the control circuit of the detection chip 220 and applied to the heating electrode of the detection chip 220 through the control circuit, so that the heating electrode releases heat and further controls the temperature of the reaction region of the detection chip 220. The reaction system solution contained in the micro-reaction chambers of the detection chip 220 performs amplification reaction at a suitable temperature.

For example, the control device 210 may be implemented as general-purpose or special-purpose hardware, software, firmware, etc., and may also include a central processing unit (CPU), an embedded processor, a programmable logic controller (PLC), etc., which is not limited by embodiments of the present disclosure.

It should be noted that in the embodiment of the present disclosure, the reaction system 200 may also include more components, such as a temperature sensor, an optical unit, a cooling unit, a communication unit, a power supply, etc., which is not limited by the embodiment of the present disclosure. For the detailed description and technical effects of the reaction system 200, reference may be made to the above description of the detection chip 100, which is not repeated here.

At least one embodiment of the present disclosure also provides a method of using the detection chip, the detection chip provided by any embodiment of the present disclosure may be operated by using the method. The method can realize high-efficiency, accurate and uniform temperature control, improve the temperature uniformity, reduce the area of the edge low-temperature region of the detection chip, effectively reduce the chip size and increase the number of micro-reaction chambers. The method provided by at least some embodiments can also realize uniform sample injection and reduce or avoid residual gas, thereby reducing or avoiding the interference of bubbles on the detection results.

Figure 16:
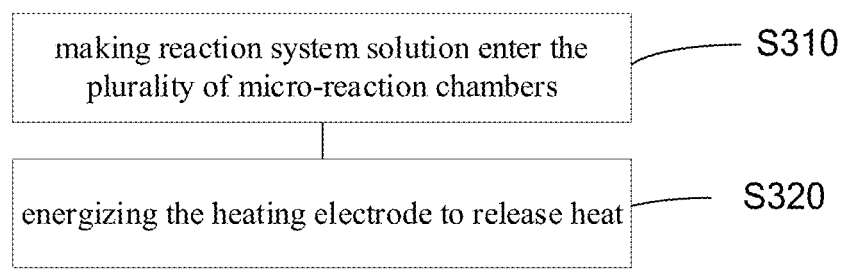
FIG. 16 is a flowchart of a method of using the detection chip provided by some embodiments of the present disclosure.

FIG. 16 is a flowchart of a method of using a detection chip provided by some embodiments of the present disclosure. For example, as shown in FIG. 16, the method includes the following operations:

At step S310: making reaction system solution enter the plurality of micro-reaction chambers 111;

At step S320: energizing the heating electrode to release heat.

For example, in the step S310, the reaction system solution may be injected into the sample injection port 31 of the detection chip 100 by a microinjection pump or a pipette, and then may enter each micro-reaction chamber 111 by self-priming liquid. For example, in the step S320, the heating electrode 12 is energized and releases heat. In some examples, in the heating electrode 12, because the resistance value of the second sub-electrode is larger than that of the first sub-electrode, the second sub-electrode releases less heat and the first sub-electrode releases more heat. In other examples, the heating electrode 12 includes a plurality of sub-electrodes, and each sub-electrode may be independently controlled so that the middle sub-electrode releases less heat and the edge sub-electrode releases more heat. Therefore, the edge heat dissipation effect can be reduced, the edge temperature of the heating electrode 12 can be increased, and the center temperature of the heating electrode 12 can be controlled not to be excessively high, thereby realizing highly efficient, accurate and uniform temperature control, improving temperature uniformity, reducing the area of the edge low-temperature region, effectively reducing the chip size and increasing the number of micro-reaction chambers. The plurality of micro-reaction chambers 111 can receive uniform heat, which is helpful to improve the accuracy of detection results.

It should be noted that in the embodiments of the present disclosure, the above-mentioned using method may further include more steps and operations, and the execution order of each step is not limited, which may be determined according to actual needs. For the detailed description and technical effect of the using method, reference may be made to the above description of the detection chip 100, which will not be repeated here.

The following statements should be noted:

(1) The accompanying drawings involve only the structure(s) in connection with the embodiment(s) of the present disclosure, and other structure(s) can be referred to common design(s).

(2) In case of no conflict, features in one embodiment or in different embodiments can be combined to obtain a new embodiment.

What are described above is related to the specific embodiments of the disclosure only and not limitative to the scope of the disclosure. The protection scope of the disclosure shall be based on the protection scope of the claims.

What is claimed is:

1. A detection chip, comprising:
   a first substrate;
   a micro-chamber definition layer, located on the first substrate and defining a plurality of micro-reaction chambers;
   a heating electrode, located on the first substrate and closer to the first substrate than the micro-chamber definition layer, configured to release heat after being energized;
   wherein the heating electrode comprises a plurality of sub-electrodes, orthographic projections of the plurality of micro-reaction chambers on the first substrate overlap with orthographic projections of at least two of the plurality of sub-electrodes on the first substrate, and the at least two of the plurality of sub-electrodes have different heating values per unit time after being energized,
   wherein the heating electrode is configured to allow a current to flow along a first direction after being energized, and the plurality of sub-electrodes are arranged at intervals along a second direction, and the second direction is perpendicular to the first direction,
   each of the plurality of sub-electrodes has two sides opposite to each other in the second direction, and the plurality of sub-electrodes comprise a first sub-electrode and at least one second sub-electrode, wherein the first sub-electrode has adjacent sub-electrode on only one of the two sides, and each of the at least one second sub-electrode has adjacent sub-electrodes on the two sides, and
   a resistance value of the second sub-electrode is larger than a resistance value of the first sub-electrode.

2. The detection chip according to claim 1, wherein a width of the second sub-electrode along the second direction is smaller than a width of the first sub-electrode along the second direction.

3. The detection chip according to claim 1, wherein a plurality of second sub-electrodes are provided, and the plurality of second sub-electrodes are arranged at intervals along the second direction,
   in the second direction, resistance values of the plurality of second sub-electrodes decrease in sequence along a direction extending from a center of the heating electrode to an edge of the heating electrode.

4. The detection chip according to claim 3, wherein in the second direction, widths of the plurality of second sub-electrodes are sequentially increased in the direction extending from the center of the heating electrode to the edge of the heating electrode.

5. The detection chip according to claim 1, wherein a plurality of second sub-electrodes are provided, and the plurality of second sub-electrodes are arranged at intervals along the second direction,
   resistance values of the plurality of second sub-electrodes are substantially equal.

6. The detection chip according to claim 1, wherein three or more sub-electrodes are provided.

7. The detection chip according to claim 1, wherein orthographic projections of the plurality of sub-electrodes on the first substrate are sequentially surrounded, and an orthographic projection of a sub-electrode except a sub-electrode located at a center of the heating electrode is annular, and the plurality of sub-electrodes are insulated from each other.

8. The detection chip according to claim 1, further comprising an accommodation chamber, wherein the plurality of micro-reaction chambers are located in the accommodation chamber, and the accommodation chamber has an arc boundary.

9. The detection chip according to claim 8, wherein the micro-chamber definition layer further defines a sample injection channel and a sample outlet channel, both of the sample injection channel and the sample outlet channel are communicated with the accommodation chamber,
the arc boundary of the accommodation chamber is located at joints of the accommodation chamber and the sample injection channel, and the accommodation chamber and the sample outlet channel, wherein a radian of the arc boundary is less than or equal to $\pi/2$,
wherein the sample injection channel and the sample outlet channel are located at opposite sides of the accommodation chamber,
the arc boundary comprises a first arc boundary and a second arc boundary, wherein the sample injection channel is communicated with the accommodation chamber at the first arc boundary, and the sample outlet channel is communicated with the accommodation chamber at the second arc boundary.

10. The detection chip according to claim 1, further comprising a control circuit layer and a first insulation layer laminated on the first substrate,
wherein the control circuit layer comprises a control circuit, the first insulation layer comprises a through hole, the heating electrode is provided on the first insulation layer, the control circuit is electrically connected with the heating electrode through the through hole, and the control circuit is configured to apply an electrical signal to the heating electrode to energize the heating electrode.

11. The detection chip according to claim 10, wherein the control circuit layer further comprises at least one connection electrode, the at least one connection electrode is not covered by the first insulation layer and exposed to air.

12. The detection chip according to claim 11, wherein in a case where the orthographic projections of the plurality of sub-electrodes on the first substrate are sequentially surrounded, a plurality of connection electrodes are provided, and the plurality of connection electrodes are divided into a plurality of groups,
a plurality of groups of connection electrodes are in one-to-one correspondence with the plurality of sub-electrodes, and each of the plurality of groups of connection electrodes is configured to transmit an electrical signal to a corresponding sub-electrode through the control circuit.

13. The detection chip according to claim 11, further comprising a reaction region and a peripheral region,
wherein the heating electrode and the plurality of micro-reaction chambers are located in the reaction region, and the connection electrode is located in the peripheral region.

14. The detection chip according to claim 1, further comprising a hydrophilic layer and a second insulation layer,
wherein the hydrophilic layer covers at least a side wall and a bottom of each of the plurality of micro-reaction chambers,
the second insulation layer is disposed between the heating electrode and the micro-chamber definition layer.

15. The detection chip according to claim 8, further comprising a second substrate and a hydrophobic layer, wherein the second substrate is provided opposite to the first substrate, wherein the hydrophobic layer covers a side of the second substrate facing the first substrate.

16. The detection chip according to claim 15, further comprising a sample injection port and a sample outlet port,
wherein the sample injection port and the sample outlet port both penetrate through the second substrate and the hydrophobic layer, and the sample injection port and the sample outlet port are located at two opposite sides of the plurality of micro-reaction chambers.

17. The detection chip according to claim 15, further comprising a bonding layer,
wherein the bonding layer is located between the first substrate and the second substrate, and a space surrounded by the bonding layer, the second substrate and the micro-chamber definition layer is the accommodation chamber,
the bonding layer is made of thermosetting adhesive or photosensitive adhesive containing a spacer.

18. A reaction system, comprising a control device and the detection chip according to claim 1,
wherein the control device is electrically connected with the detection chip and is configured to apply an electrical signal to the detection chip.

19. A method of using the detection chip according to claim 1, comprising:
making reaction system solution enter the plurality of micro-reaction chambers;
energizing the heating electrode to release heat.

* * * * *